US008628930B2

(12) United States Patent
Saito et al.

(10) Patent No.: US 8,628,930 B2
(45) Date of Patent: *Jan. 14, 2014

(54) USE OF MEGALIN IN URINE AS MARKER FOR DETECTING RENAL DISORDER

(75) Inventors: Akihiko Saito, Niigata (JP); Yasuhiko Tomino, Bunkyo-ku (JP); Katsuhiko Asanuma, Bunkyo-ku (JP); Shinya Ogasawara, Gosen (JP); Hiroyuki Kurosawa, Gosen (JP); Yoshiaki Hirayama, Gosen (JP)

(73) Assignees: Niigata University, Niigata (JP); Juntendo Education Foundation, Tokyo (JP); Denka Seiken Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/266,397

(22) PCT Filed: Apr. 27, 2010

(86) PCT No.: PCT/JP2010/057490
§ 371 (c)(1),
(2), (4) Date: Oct. 26, 2011

(87) PCT Pub. No.: WO2010/126055
PCT Pub. Date: Nov. 4, 2010

(65) Prior Publication Data
US 2012/0058489 A1    Mar. 8, 2012

(30) Foreign Application Priority Data

Apr. 27, 2009 (JP) .................................. 2009-108493

(51) Int. Cl.
*G01N 33/53* (2006.01)
(52) U.S. Cl.
USPC ........................................................ 435/7.1
(58) Field of Classification Search
None
See application file for complete search history.

(56) References Cited

U.S. PATENT DOCUMENTS

| 7,955,809 | B2 * | 6/2011 | Ogasawara et al. ............ 435/7.1 |
| 2004/0204357 | A1 | 10/2004 | Brautigam et al. |
| 2004/0235161 | A1 | 11/2004 | Tabata et al. |
| 2009/0117594 | A1 | 5/2009 | Ogasawara et al. |
| 2010/0233738 | A1 | 9/2010 | Hara et al. |

FOREIGN PATENT DOCUMENTS

| EP | 2 006 683 A1 | 12/2008 |
| EP | 2 426 495 A1 | 3/2012 |
| JP | 04-351962 | 12/1992 |
| JP | 08-105889 | 4/1996 |
| JP | 2005-528615 A | 9/2005 |
| JP | 2007-263750 A | 10/2007 |
| JP | 2007-536260 A | 12/2007 |
| JP | 2009-511913 A | 3/2009 |
| WO | WO-03/102493 A1 | 12/2003 |
| WO | WO-03/102593 A1 | 12/2003 |
| WO | WO-2005/107793 A2 | 11/2005 |
| WO | WO-2007/047458 A2 | 4/2007 |
| WO | WO-2009/041577 A1 | 4/2009 |
| WO | WO-2009/117594 A1 | 4/2009 |

OTHER PUBLICATIONS

Norden et al. J Am. Soc. Nephrol. 2002 vol. 13, p. 125-133.*
Kuusniemi et al. Kidney International 2005 vol. 68, p. 121-132.*
Akihiko Saito et al., "Megalin, a Multiligand Endocytotic Receptor: The Role in the Development of Diabetic Nephropathy, Metabolic Syndrome—related Nephropathy and Uremia", Niigata Medical Journal, 119(1), Jan. 10, 2005, pp. 1-5.
International Search Report PCT/JP2010/057490 dated Jun. 8, 2010.
Jakub Gburek et al., "Renal uptake of myoglobin is mediated by the endocytic receptors megalin and cubilin", Am J Physiol Renal Physiol 285: F451-F458, 2003.
De Jong, M. et al., "Megalin Is Essential for Renal Proximal Tubule Reabsorption of 111In-DTPA-Octreotide", The Journal of Nuclear Medicine, vol. 46, No. 10, Oct. 2005, pp. 1696-1700.
EP Application No. 10769741.9, Search Report Dated Jan. 9, 2013.
Final Office Action in U.S. Appl. No. 13/093,984 dated Aug. 6, 2013.
Final Office Action U.S. Appl. No. 12/293,992 dated Aug. 19, 2010.
http://www.abcam.com/index.html?t=115434&pt=1downloaded Mar. 21, 2011.
http://www.biognosisltd.co.uk/Exocell/Urinary%20Assays.htmldownloaded Mar. 21, 2011.
Ilse Raats et al., "Reduction in Glomerular Heparan Sulfate Correlates with Complement Deposition and Albuminuria in Active Heymann Nephritis", J. Am. Soc. Nephrol. 10: 1689-1699, 1999.
International Search Report in PCT/JP2007/056660 dated May 15, 2007.
International Search Report PCT/JP2010/057465 dated Aug. 3, 2010.
Jordan (The Protein Protocol Handbook, second edition, edited by Walker, year 2000, p. 1083-1088).
Knox M.D. et al., HIV and community. Mental Healthcare. The Johns Hopkins University Press Ltd., London, 1998, p. 25.
Kobayashi et al., "Conditions for Solubilization of Tamm-Horsfall Protein/Uromodulin in Human Urine and Establishment of a Sensitive and Accurate Enzyme-Linked Immunosorbent Assay (ELISA) Method", Archives of Biochemistry and Biophysics, vol. 388, No. 1, Apr. 1, 2001, pp. 113-120.
Kuusniemi et al., "Kidneys with heavy proteinuria show fibrosis, inflammation, and oxidative stress, but no tubular phenotypic change", Kidney International, vol. 68, (2005) pp. 121-132.

(Continued)

*Primary Examiner* — Jacob Cheu
(74) *Attorney, Agent, or Firm* — Foley & Lardner LLP

(57) ABSTRACT

This invention provides a simple means for detecting a renal disorder, a diagnostic marker for a renal disorder that enables prognostic prediction of a renal disorder (e.g., diabetic nephropathy and IgA nephropathy) and evaluation of the degree of nephropathy at the phase of stage-II diabetic nephropathy by measuring the megalin level in urine associated with a renal disorder used for the detection means, and use of such marker. The invention also provides the use of human megalin obtained from the urine sample of a subject as a marker for detecting a renal disorder.

5 Claims, 8 Drawing Sheets

(56) References Cited

OTHER PUBLICATIONS

Non-Final Office Action U.S. Appl. No. 12/293,992 dated Dec. 15, 2009.
Non-Final Office Action U.S. Appl. No. 12/293,992 dated Sep. 28, 2009.
Non-final office action U.S. Appl. No. 13/093,984 dated Jan. 12, 2012.
Notice of Allowance U.S. Appl. No. 12/293,992 dated Feb. 8, 2011.
Office Action in JP Appln No. 2009-108498 dated Jul. 30, 2013.
Russian Office Action Application No. 2008142534/15 (055325) w/English translation, dated 2012.
Saito et al., "Megalin, a Multiligand Endocytotic Receptor: The Role in the Development of Diabetic Nephropathy, Metabolic Syndrome—related Nephropathy and Uremia", Niigata Medical Journal, 119(1), Jan. 10, 2005, pp. 1-5.
Supplementary Search Report in EP 07 74 0098 dated Aug. 24, 2009.
Thrailkill, K.M. et al., "Microalbuminuria in Type 1 Diabetes is Associated With Enhanced Excretion of the Endocytic Multiligand Receptors Megalin and Cubilin", Diabetes Care, vol. 32, No. 7, Apr. 14, 2009, p. 1266-1268.
Van Venrooij, W.J. et al., Manual of Biological Markers of Disease, Kluwer Academic Publishers, the Netherlands, 1993, vol. 1, AMAN-C1.1/5.
Willnow et al. (PNAS 1996 vol. 93 p. 8460-8464).
Yamazaki et al., "All Four Putative Ligand-Binding Domains in Megalin Contain Pathogenic Epitopes Capable of Inducing Passive Heymann Nephritis", J. Am. Soc. Nephroi., 1998, vol. 9, 1638-1644.
EP Application No. 10769753.4, Search Report dated Feb. 11, 2013.
Norden, A G W et al., "Urinary Megalin Deficiency Inplicates Abnormal Tubular Endocytic Function in Fanconi Syndrome", Journal of the American Society of Nephrology, Williams and Wilkins, Baltimore, MD, US, vol. 13, Jan. 1, 2002, pp. 125-133.
Ogasawara, Shinya et al., "Significance of Urinary Full-Legnth and Ectodomain Forms of Megalin in Patients With Type 2 Diabetes.", Diabetes Care May 2012 LNKD-PUBMED: 22410816, vol. 35, No. 5, May 2012, pp. 1112-1118.
Thrailkill, K.M. et al., "Microalbuminuria in Type 1 Diabetes is Associated With Enhanced Excretion of the Endocytic Multiligand Receptors Megalin and Cubilin", Diabetes Care, vol. 32, No. 7, Apr. 14, 2009, pp. 1266-1268.
Wilmer, Martijn et al., "Urinary Protein Excretion Pattern and Renal Expression of Megalin and Cubilin in Nephropathic Cystinosis.", American Journal of Kidney Diseases, vol. 51, Jan. 1, 2008, pp. 893-903.

* cited by examiner

SEQUENCE LISTING

<160> NUMBER OF SEQ ID NOS: 2

<210> SEQ ID NO 1
<211> LENGTH: 13968
<212> TYPE: DNA
<213> ORGANISM: Homo sapiens

<400> SEQUENCE: 1

```
atggatcgcg ggccggcagc agtggcgtgc acgctgctcc tggctctcgt cgcctgccta      60
gcgccggcca gtggccaaga atgtgacagt gcgcattttc gctgtggaag tgggcattgc     120
atccctgcag actggaggtg tgatgggacc aaagactgtt cagatgacgc ggatgaaatt     180
ggctgcgctg ttgtgacctg ccagcagggc tatttcaagt gccagagtga gggacaatgc     240
atccccagct cctgggtgtg tgaccaagat caagactgtg atgatggctc agatgaacgt     300
caagattgct cacaaagtac atgctcaagt catcagataa catgctccaa tggtcagtgt     360
atcccaagtg aatacaggtg cgaccacgtc agagactgcc ccgatggagc tgatgagaat     420
gactgccagt acccaacatg tgagcagctt acttgtgaca atggggcctg ctataacacc     480
agtcagaagt gtgattggaa agttgattgc agggactcct cagatgaaat caactgcact     540
gagatatgct tgcacaatga gttttcatgt ggcaatggag agtgtatccc tcgtgcttat     600
gtctgtgacc atgacaatga ttgccaagac ggcagtgatg aacatgcttg caactatccg     660
```

```
acctgcggtg gttaccagtt cacttgcccc agtggccgat gcattatca aaactgggtt    720 tgtgatggag aagatgactg taaagataat ggagatgaag atggatgtga aagcggtcct    780
catgatgttc ataaatgttc cccaagagaa tggtcttgcc cagagtcggg acgatgcatc    840
tccatttata aagtttgtga tgggatttta gattgcccag gaagagaaga tgaaaacaac    900
actagtaccg gaaaatactg tagtatgact ctgtgctctg ccttgaactg ccagtaccag    960
tgccatgaga cgccgtatgg aggagcgtgt ttttgtcccc caggttatat catcaaccac   1020
aatgacagcc gtacctgtgt tgagtttgat gattgccaga tatggggaat tgtgaccag   1080 aagtgtgaaa gccgacctgg ccgtcacctg tgccactgtg aagaagggta tatcttggag   1140
cgtggacagt attgcaaagc taatgattcc tttggcgagg cctccattat cttctccaat   1200
ggtcgggatt tgttaattgg tgatattcat ggaaggagct ccggatcct agtggagtct   1260 cagaatcgtg gagtggccgt gggtgtggct ttccactatc acctgcaaag agttttttgg   1320
acagacaccg tgcaaaataa ggttttttca gttgacatta atggtttaaa tatccaagag   1380
gttctcaatg tttctgttga aaccccagag aacctggctg tggactgggt taataataaa   1440
atctatctag tggaaaccaa ggtcaaccgc atagatatgg taaatttgga tggaagctat   1500
cgggttaccc ttataactga aaacttgggg catcctagag gaattgccgt ggacccaact   1560
gttggttatt tatttttctc agattgggag agccttctg gggaacctaa gctgaaaagg   1620
gcattcatgg atggcagcaa ccgtaaagac ttggtgaaaa caaagctggg atggcctgct   1680
ggggtaactc tggatatgat atcgaagcgt gtttactggg ttgactctcg gtttgattac   1740
attgaaactg taacttatga tggaattcaa aggaagactg tagttcatgg aggctccctc   1800
attcctcatc cctttggagt aagcttattt gaaggtcagg tgttctttac agattggaca   1860
aagatggccg tgctgaaggc aaacaagttc acagagacca acccacaagt gtactaccag   1920
gcttccctga ggcccatgg agtgactgtt taccattccc tcagacagcc ctatgctacc   1980
aatccgtgta aagataacaa tgggggctgt gagcaggtct gtgttctcag ccacagaaca   2040
gataatgatg gtttggggttt ccgttgcaag tgcacattcg gcttccaact ggatacagat   2100
gagcgccact gcattgctgt tcagaatttc ctcattttt catcccaagt tgctattcgt   2160
gggatcccgt tcaccttgtc tacccaggaa gatgtcatgg ttccagtttc ggggaatcct   2220
tctttctttg tcgggattga ttttgacgcc caggacagca ctatcttttt ttcagatatg   2280
tcaaaacaca tgattttaa gcaaaagatt gatggcacag gaagagaaat tctcgcagct   2340
aacagggtgg aaaatgttga aagtttggct tttgattgga tttcaagaa tctctattgg   2400 acagactctc attacaagag tatcagtgtc atgaggctag ctgataaaac gagacgcaca   2460
gtagttcagt atttaaataa cccacggtcg gtggtagttc atccttttgc cgggtatcta   2520
ttcttcactg attggttccg tcctgctaaa attatgagag catggagtga cggatctcac   2580
ctcttgcctg taataaacac tactcttgga tgcccaatg gcttggccat cgattgggct   2640
gcttcacgat tgtactgggt agatgcctat tttgataaaa ttgagcacag cacctttgat   2700
ggtttagaca gaagaagact gggccatata gagcagatga cacatccgtt tggacttgcc   2760
atctttggag agcatttatt ttttactgac tggagactgg gtgccattat tcgagtcagg   2820
aaagcagatg gtggagaaat gacagttatc cgaagtggca ttgcttacat actgcatttg   2880
aaatcgtatg atgtcaacat ccagactggt tctaacgcct gtaatcaacc cacgcatcct   2940
aacggtgact gcagccactt ctgcttcccg gtgccaaatt ccagcgagt gtgtgggtgc   3000 ccttatggaa tgaggctggc ttccaatcac ttgacatgcg agggggaccc aaccaatgaa   3060
```

```
ccacccacgg agcagtgtgg cttatttttcc ttcccctgta aaaatggcag atgtgtgccc    3120
aattactatc tctgtgatgg agtcgatgat tgtcatgata acagtgatga gcaactatgt    3180
ggcacactta ataatacctg ttcatcttcg gcgttcacct gtggccatgg ggagtgcatt    3240
cctgcacact ggcgctgtga caaacgcaac gactgtgtgg atggcagtga tgagcacaac    3300
tgccccaccc acgcacctgc ttcctgcctt gacacccaat acacctgtga taatcaccag    3360
tgtatctcaa agaactgggt ctgtgacaca gacaatgatt gtggggatgg atctgatgaa    3420
aagaactgca attcgacaga gacatgccaa cctagtcagt ttaattgccc caatcatcga    3480
tgtattgacc tatcgtttgt ctgtgatggt gacaaggatt gtgttgatgg atctgatgag    3540
gttggttgtg tattaaactg tactgcttct caattcaagt gtgccagtgg ggataaatgt    3600
attggcgtca caaatcgttg tgatggtgtt tttgattgca gtgacaactc ggatgaagcg    3660
ggctgtccaa ccaggcctcc tggtatgtgc cactcagatg aatttcagtg ccaagaagat    3720
ggtatctgca tcccgaactt ctgggaatgt gatgggcatc cagactgcct ctatggatct    3780
gatgagcaca atgcctgtgt ccccaagact tgcccttcat catatttcca ctgtgacaac    3840
ggaaactgca tccacagggc atggctctgt gatcgggaca atgactgcgg ggatatgagt    3900
gatgagaagg actgccctac tcagcccttt cgctgtccta gttggcaatg gcagtgtctt    3960
ggccataaca tctgtgtgaa tctgagtgta gtgtgtgatg catctttga ctgccccaat    4020 gggacagatg agtccccact ttgcaatggg aacagctgct cagatttcaa tggtggttgt    4080
actcacgagt gtgttcaaga gccctttggg gctaaatgcc tatgtccatt gggattctta    4140
cttgccaatg attctaagac ctgtgaagac atagatgaat gtgatattct aggctcttgt    4200
agccagcact gttacaatat gagaggttct ttccggtgct cgtgtgatac aggctacatg    4260
ttagaaagtg atgggaggac ttgcaaagtt acagcatctg agagtctgct gttacttgtg    4320
gcaagtcaga acaaaattat tgccgacagt gtcacctccc aggtccacaa tatctattca    4380
ttggtcgaga atggttctta cattgtagct gttgattttg attcaattag tggtcgtatc    4440
ttttggtctg atgcaactca gggtaaaacc tggagtgcgt ttcaaaatgg aacggacaga    4500
agagtggtat ttgacagtag catcatcttg actgaaacta ttgcaataga ttgggtaggt    4560
cgtaatcttt actggacaga ctatgctctg gaaacaattg aagtctccaa aattgatggg    4620
agccacagga ctgtgctgat tagtaaaaac ctaacaaatc caagaggact agcattagat    4680
cccagaatga atgagcatct actgttctgg tctgactggg gccaccaccc tcgcatcgag    4740
cgagccagca tggacggcag catgcgcact gtcattgtcc aggacaagat cttctggccc    4800
tgcggcttaa ctattgacta ccccaacaga ctgctctact tcatggactc ctatcttgat    4860
tacatggact tttgcgatta taatggacac catcggagac aggtgatagc cagtgatttg    4920
attatacggc accccatgc cctaactctc tttgaagact ctgtgtactg gactgaccgt    4980
gctactcgtc gggttatgcg agccaacaag tggcatggag ggaaccagtc agttgtaatg    5040
tataatattc aatggcccct tgggattgtt gcggttcatc cttcgaaaca accaaattcc    5100
gtgaatccat gtgccttttc ccgctgcagc catctctgcc tgctttcctc acaggggcct    5160 cattttact cctgtgtttg tccttcagga tggagtctgt ctcctgatct cctgaattgc    5220
ttgagagatg atcaaccttt cttaataact gtaaggcaac atataatttt tggaatctcc    5280
cttaatcctg aggtgaagag caatgatgct atggtcccca tgcagggat acagaatggt    5340 ttagatgttg aatttgatga tgctgagcaa tacatctatt gggttgaaaa tccaggtgaa    5400
attcacagag tgaagacaga tggcaccaac aggacagtat ttgcttctat atctatggtg    5460
```

```
gggccttcta tgaacctggc cttagattgg atttcaagaa acctttattc taccaatcct   5520
agaactcagt caatcgaggt tttgacactc cacggagata tcagatacag aaaaacattg   5580
attgccaatg atgggacagc tcttggagtt ggctttccaa ttggcataac tgttgatcct   5640
gctcgtggga agctgtactg gtcagaccaa ggaactgaca gtggggttcc tgccaagatc   5700
gccagtgcta acatggatgg cacatctgtg aaaactctct ttactgggaa cctcgaacac   5760
ctggagtgtg tcactcttga catcgaagag cagaaactct actgggcagt cactggaaga   5820
ggagtgattg aaagaggaaa cgtggatgga acagatcgga tgatcctggt acaccagctt   5880
tcccacccct ggggaattgc agtccatgat tctttccttt attatactga tgaacagtat   5940
gaggtcattg aaagagttga taaggccact ggggccaaca aaatagtctt gagagataat   6000
gttccaaatc tgagggggtct tcaagtttat cacagacgca atgccgccga atcctcaaat   6060
ggctgtagca acaacatgaa tgcctgtcag cagatttgcc tgcctgtacc aggaggattg   6120
ttttcctgcg cctgtgccac tggatttaaa ctcaatcctg ataatcggtc ctgctctcca   6180
tataactctt tcattgttgt ttcaatgctg tctgcaatca gaggctttag cttggaattg   6240
tcagatcatt cagaaaccat ggtgccggtg gcaggccaag gacgaaacgc actgcatgtg   6300
gatgtggatg tgtcctctgg ctttatttat ggtgtgatt ttagcagctc agtggcatct   6360
gataatgcga tccgtagaat taaaccagat ggatcttctc tgatgaacat tgtgacacat   6420
ggaataggag aaaatggagt ccggggtatt gcagtggatt gggtagcagg aaatctttat   6480
ttcaccaatg cctttgtttc tgaaacactg atagaagttc tgcggatcaa tactacttac   6540
cgccgtgttc ttcttaaagt cacagtggac atgcctaggc atattgttgt agatcccaag   6600
aacagatacc tcttctgggc tgactatggg cagagaccaa agattgagcg ttctttcctt   6660
gactgtacca atcgaacagt gcttgtgtca gagggcattg tcacaccacg gggcttggca   6720
gtggaccgaa gtgatggcta cgtttattgg gttgatgatt cttttagatat aattgcaagg   6780 attcgtatca atggagagaa ctctgaagtg attcgttatg gcagtcgtta cccaactcct   6840
tatggcatca ctgttttga aaattctatc atatgggtag ataggaattt gaaaaagatc   6900
ttccaagcca gcaaggaacc agagaacaca gagccaccca cagtgataag agacaatatc   6960
aactggctaa gagatgtgac catctttgac aagcaagtcc agccccggtc accagcagag   7020
gtcaacaaca accccttgctt ggaaaacaat ggtgggtgct ctcatctctg ctttgctctg   7080
cctggattgc acaccccaaa atgtgactgt gcctttggga ccctgcaaag tgatggcaag   7140
aattgtgcca tttcaacaga aaatttcctc atctttgcct tgtctaattc cttgagaagc   7200
ttacacttgg accctgaaaa ccatagccca ccttttccaaa caataaatgt ggaaagaact   7260
gtcatgtctc tagactatga cagtgtaagt gatagaatct acttcacaca aaatttagcc   7320
tctggagttg gacagatttc ctatgccacc ctgtcttcag ggatccatac tccaactgtc   7380
attgcttcag gtatagggac tgctgatggc attgcctttg actggattac tagaagaatt   7440
tattacagtg actacctcaa ccagatgatt aattccatgg ctgaagatgg gtctaaccgc   7500
actgtgatag cccgcgttcc aaaaccaaga gcaattgtgt tagatccctg ccaagggtac   7560
ctgtactggg ctgactggga tacacatgcc aaaatcgaga gagccacatt gggaggaaac   7620
ttccgggtac ccattgtgaa cagcagtctg gtcatgccca gtgggctgac tctggactat   7680
gaagaggacc ttctctactg ggtggatgct agtctgcaga ggattgaacg cagcactctg   7740
acgggcgtgg atcgtgaagt cattgtcaat gcagccgttc atgctttgg cttgactctc   7800 tatggccagt atatttactg gactgacttg tacacacaaa gaatttaccg agctaacaaa   7860
```

```
tatgacgggt caggtcagat tgcaatgacc acaaatttgc tctcccagcc caggggaatc      7920
aacactgttg tgaagaacca gaaacaacag tgtaacaatc cttgtgaaca gtttaatggg      7980
ggctgcagcc atatctgtgc accaggtcca aatggtgccg agtgccagtg tccacatgag      8040
ggcaactggt atttggccaa caacaggaag cactgcattg tggacaatgg tgaacgatgt      8100
ggtgcatctt ccttcacctg ctccaatggg cgctgcatct cggaagagtg gaagtgtgat      8160
aatgacaacg actgtgggga tggcagtgat gagatggaaa gtgtctgtgc acttcacacc      8220
tgctcaccga cagccttcac ctgtgccaat gggcgatgtg tccaatactc ttaccgctgt      8280
gattactaca atgactgtgg tgatggcagt gatgaggcag ggtgcctgtt cagggactgc      8340
aatgccacca cggagtttat gtgcaataac agaaggtgca tacctcgtga gtttatctgc      8400
aatggtgtag acaactgcca tgataataac acttcagatg agaaaaattg ccctgatcgc      8460
acttgccagt ctggatacac aaaatgtcat aattcaaata tttgtattcc tcgcgtttat      8520
ttgtgtgacg gagacaatga ctgtggagat aacagtgatg aaaaccctac ttattgcacc      8580
actcacacat gcagcagcag tgagttccaa tgcgcatctg gcgctgtat tcctcaacat      8640
tggtattgtg atcaagaaac agattgtttt gatgcctctg atgaacctgc ctcttgtggt      8700
cactctgagc gaacatgcct agctgatgag ttcaagtgtg atggtgggag gtgcatccca      8760
agcgaatgga tctgtgacgg tgataatgac tgtgggata tgagtgacga ggataaaagg      8820
caccagtgtc agaatcaaaa ctgctcggat tccgagtttc tctgtgtaaa tgacagacct      8880
ccggacagga ggtgcattcc ccagtcttgg gtctgtgatg cgatgtgga ttgtactgac      8940
ggctacgatg agaatcagaa ttgcaccagg agaacttgct ctgaaaatga attcacctgt      9000
ggttacggac tgtgtatccc aaagatattc aggtgtgacc ggcacaatga ctgtggtgac      9060
tatagcgacg agaggggctg cttataccag acttgccaac agaatcagtt tacctgtcag      9120
aacgggcgct gcattagtaa aaccttcgtc tgtgatgagg ataatgactg tggagacgga      9180
tctgatgagc tgatgcacct gtgccacacc ccagaaccca cgtgtccacc tcacgagttc      9240
aagtgtgaca atgggcgctg catcgagatg atgaaactct gcaaccacct agatgactgt      9300
ttggacaaca gcgatgagaa aggctgtggc attaatgaat gccatgaccc ttcaatcagt      9360
ggctgcgatc acaactgcac agacaccta accagtttct attgttcctg tcgtcctggt      9420
tacaagctca tgtctgacaa gcggacttgt gttgatattg atgaatgcac agagatgcct      9480
tttgtctgta gccagaagtg tgagaatgta ataggctcct acatctgtaa gtgtgcccca      9540
ggctacctcc gagaaccaga tggaaagacc tgccggcaaa acagtaacat cgaaccctat      9600
ctcattttta gcaaccgtta ctatttgaga aatttaacta tagatggcta tttttactcc      9660
ctcatcttgg aaggactgga caatgttgtg gcattagatt tgaccgagt agagaagaga      9720
ttgtattgga ttgatacaca gaggcaagtc attgagagaa tgtttctgaa taagacaaac      9780
aaggagacaa tcataaacca cagactacca gctgcagaaa gtctggctgt agactgggtt      9840
tccagaaagc tctactggtt ggatgcccgc ctggatggcc tctttgtctc tgacctcaat      9900
ggtggacacc gccgcatgct ggcccagcac tgtgtggatg ccaacaacac cttctgcttt      9960
gataatccca gggacttgc ccttcaccct caatatgggt acctctactg ggcagactgg     10020
ggtcaccgcg catacattgg gagagtaggc atggatggaa ccaacaagtc tgtgataatc     10080
tccaccaagt tagagtggcc taatggcatc accattgatt acaccaatga tctactctac     10140
tgggcagatg cccacctggg ttacatagag tactctgatt tggagggcca ccatcgcaca     10200
acggtgtatg atgggggcact gcctcacccct ttcgctatta ccattttga agacactatt     10260
```

```
tattggacag attggaatac aaggacagtg gaaaagggaa acaaatatga tggatcaaat    10320
agacagacac tggtgaacac aacacacaga ccatttgaca tccatgtgta ccatccatat    10380
aggcagccca ttgtgagcaa tccctgtggt accaacaatg gtggctgttc tcatctctgc    10440
ctcatcaagc caggaggaaa agggttcact tgcgagtgtc cagatgactt ccgcacccct    10500
caactgagtg gcagcaccta ctgcatgccc atgtgctcca gcacccagtt cctgtgcgct    10560
aacaatgaaa agtgcattcc tatctggtgg aaatgtgatg gacagaaaga ctgctcagat    10620
ggctctgatg aactggccct ttgcccgcag cgcttctgcc gactgggaca gttccagtgc    10680
agtgacggca actgcaccag cccgcagact ttatgcaatg ctcaccaaaa ttgccctgat    10740
gggtctgatg aagaccgtct tctttgtgag aatcaccact gtgactccaa tgaatggcag    10800
tgcgccaaca aacgttgcat cccagaatcc tggcagtgtg acacatttaa cgactgtgag    10860
gataactcag atgaagacag ttcccactgt gccagcagga cctgccggcc gggccagttt    10920
cggtgtgcta atggccgctg catcccgcag gcctggaagt gtgatgtgga taatgattgt    10980
ggagaccact cggatgagcc cattgaagaa tgcatgagct ctgcccatct ctgtgacaac    11040
ttcacagaat tcagctgcaa acaaattac cgctgcatcc caaagtgggc cgtgtgcaat    11100
```

-continued

```
aacatcctgg ttttcgagga ccttggttgg ccaactggcc tttctatcga ttatttgaac   12720
aatgaccgaa tctactggag tgacttcaag gaggacgtta ttgaaaccat aaaatatgat   12780
gggactgata ggagagtcat tgcaaaggaa gcaatgaacc cttacagcct ggacatcttt   12840
gaagaccagt tatactggat atctaaggaa aagggagaag tatggaaaca aaataaattt   12900
gggcaaggaa agaaagagaa aacgctggta gtgaaccctt ggctcactca agttcgaatc   12960
tttcatcaac tcagatacaa taagtcagtg cccaaccttt gcaaacagat ctgcagccac   13020
ctctgccttc tgagacctgg aggatacagc tgtgcctgtc cccaaggctc agctttata   13080 gaggggagca ccactgagtg tgatgcagcc atcgaactgc ctatcaacct gccccccca   13140 tgcaggtgca tgcacggagg aaattgctat tttgatgaga ctgacctccc caaatgcaag   13200
tgtcctagcg gctacaccgg aaaatattgt gaaatggcgt tttcaaaagg catctctcca   13260
ggaacaaccg cagtagctgt gctgttgaca atcctcttga tcgtcgtaat tggagctctg   13320
gcaattgcag gattcttcca ctatagaagg accggctccc ttttgcctgc tctgcccaag   13380
ctgccaagct taagcagtct cgtcaagccc tctgaaaatg ggaatggggt gaccttcaga   13440
tcaggggcag atcttaacat ggatattgga gtgtctggtt ttggacctga dactgctatt   13500
gacaggtcaa tggcaatgag tgaagacttt gtcatggaaa tggggaagca gcccataata   13560
tttgaaaacc caatgtactc agccagagac agtgctgtca agtggttca gccaatccag   13620 gtgactgtat ctgaaaatgt ggataataag aattatggaa gtcccataaa cccttctgag   13680
atagttccag agacaaaccc aacttccacca gctgctgatg aactcaggt gacaaaatgg   13740 aatctcttca acgaaaatc taaacaaact accaactttg aaaatccaat ctatgcacag   13800
atggagaacg agcaaaagga aagtgttgct gcgacaccac ctccatcacc ttcgctccct   13860
gctaagccta agcctccttc gagaagagac ccaactccaa cctattctgc aacagaagac   13920
acttttaaag acaccgcaaa tcttgttaaa gaagactctg aagtatag                13968
```

<210> SEQ ID NO 2
<211> LENGTH: 4655
<212> TYPE: PRT
<213> ORGANISM: Homo sapiens

<400> SEQUENCE: 2

```
Met Asp Arg Gly Pro Ala Ala Val Ala Cys Thr Leu Leu Leu Ala Leu
 1               5                  10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
            35                  40                  45

Gly Thr Lys Asp Cys Ser Asp Asp Ala Asp Glu Ile Gly Cys Ala Val
        50                  55                  60

Val Thr Cys Gln Gln Gly Tyr Phe Lys Cys Gln Ser Glu Gly Gln Cys
    65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
               100                 105                 110

Ile Thr Cys Ser Asn Gly Gln Cys Ile Pro Ser Glu Tyr Arg Cys Asp
           115                 120                 125

His Val Arg Asp Cys Pro Asp Gly Ala Asp Glu Asn Asp Cys Gln Tyr
       130                 135                 140
```

-continued

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
            165                 170                 175

Ile Asn Cys Thr Glu Ile Cys Leu His Asn Glu Phe Ser Cys Gly Asn
        180                 185                 190

Gly Glu Cys Ile Pro Arg Ala Tyr Val Cys Asp His Asp Asn Asp Cys
    195                 200                 205

Gln Asp Gly Ser Asp Glu His Ala Cys Asn Tyr Pro Thr Cys Gly Gly
210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
            260                 265                 270

Cys Pro Glu Ser Gly Arg Cys Ile Ser Ile Tyr Lys Val Cys Asp Gly
        275                 280                 285

Ile Leu Asp Cys Pro Gly Arg Glu Asp Glu Asn Asn Thr Ser Thr Gly
    290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
            340                 345                 350

Gln Ile Trp Gly Ile Cys Asp Gln Lys Cys Glu Ser Arg Pro Gly Arg
        355                 360                 365

His Leu Cys His Cys Glu Glu Gly Tyr Ile Leu Glu Arg Gly Gln Tyr
    370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
            420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
    450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
    530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

```
Arg Phe Asp Tyr Ile Glu Thr Val Thr Tyr Asp Gly Ile Gln Arg Lys
                580                 585                 590

Thr Val Val His Gly Gly Ser Leu Ile Pro His Pro Phe Gly Val Ser
                595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
                660                 665                 670

Val Cys Val Leu Ser His Arg Thr Asp Asn Asp Gly Leu Gly Phe Arg
                675                 680                 685

Cys Lys Cys Thr Phe Gly Phe Gln Leu Asp Thr Asp Glu Arg His Cys
                690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
                740                 745                 750

Ser Thr Ile Phe Phe Ser Asp Met Ser Lys His Met Ile Phe Lys Gln
                755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
                820                 825                 830

Val His Pro Phe Ala Gly Tyr Leu Phe Phe Thr Asp Trp Phe Arg Pro
                835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Leu Gly His Ile Glu Gln
                900                 905                 910

Met Thr His Pro Phe Gly Leu Ala Ile Phe Gly Glu His Leu Phe Phe
                915                 920                 925

Thr Asp Trp Arg Leu Gly Ala Ile Ile Arg Val Arg Lys Ala Asp Gly
                930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
                980                 985                 990

Asn Phe Gln Arg Val Cys Gly Cys Pro Tyr Gly Met Arg Leu Ala Ser
```

```
                995              1000            1005
Asn His Leu Thr Cys Glu Gly Asp Pro Thr Asn Glu Pro Pro Thr Glu
1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ala Phe
                1060                1065                1070

Thr Cys Gly His Gly Glu Cys Ile Pro Ala His Trp Arg Cys Asp Lys
                1075                1080                1085

Arg Asn Asp Cys Val Asp Gly Ser Asp Glu His Asn Cys Pro Thr His
                1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
                1125                1130                1135

Gly Ser Asp Glu Lys Asn Cys Asn Ser Thr Glu Thr Cys Gln Pro Ser
                1140                1145                1150

Gln Phe Asn Cys Pro Asn His Arg Cys Ile Asp Leu Ser Phe Val Cys
                1155                1160                1165

Asp Gly Asp Lys Asp Cys Val Asp Gly Ser Asp Glu Val Gly Cys Val
                1170                1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
                1205                1210                1215

Ser Asp Glu Ala Gly Cys Pro Thr Arg Pro Pro Gly Met Cys His Ser
                1220                1225                1230

Asp Glu Phe Gln Cys Gln Glu Asp Gly Ile Cys Ile Pro Asn Phe Trp
                1235                1240                1245

Glu Cys Asp Gly His Pro Asp Cys Leu Tyr Gly Ser Asp Glu His Asn
                1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
                1285                1290                1295

Gly Asp Met Ser Asp Glu Lys Cys Pro Thr Gln Pro Phe Arg Cys
                1300                1305                1310

Pro Ser Trp Gln Trp Gln Cys Leu Gly His Asn Ile Cys Val Asn Leu
                1315                1320                1325

Ser Val Val Cys Asp Gly Ile Phe Asp Cys Pro Asn Gly Thr Asp Glu
                1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
                1365                1370                1375

Leu Gly Phe Leu Leu Ala Asn Asp Ser Lys Thr Cys Glu Asp Ile Asp
                1380                1385                1390

Glu Cys Asp Ile Leu Gly Ser Cys Ser Gln His Cys Tyr Asn Met Arg
                1395                1400                1405

Gly Ser Phe Arg Cys Ser Cys Asp Thr Gly Tyr Met Leu Glu Ser Asp
                1410                1415                1420
```

```
Gly Arg Thr Cys Lys Val Thr Ala Ser Glu Ser Leu Leu Leu Val
1425                1430                1435                1440

Ala Ser Gln Asn Lys Ile Ile Ala Asp Ser Val Thr Ser Gln Val His
            1445                1450                1455

Asn Ile Tyr Ser Leu Val Glu Asn Gly Ser Tyr Ile Val Ala Val Asp
        1460                1465                1470

Phe Asp Ser Ile Ser Gly Arg Ile Phe Trp Ser Asp Ala Thr Gln Gly
    1475                1480                1485

Lys Thr Trp Ser Ala Phe Gln Asn Gly Thr Asp Arg Arg Val Val Phe
1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
            1525                1530                1535

Lys Ile Asp Gly Ser His Arg Thr Val Leu Ile Ser Lys Asn Leu Thr
        1540                1545                1550

Asn Pro Arg Gly Leu Ala Leu Asp Pro Arg Met Asn Glu His Leu Leu
    1555                1560                1565

Phe Trp Ser Asp Trp Gly His His Pro Arg Ile Glu Arg Ala Ser Met
1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
            1605                1610                1615

Ser Tyr Leu Asp Tyr Met Asp Phe Cys Asp Tyr Asn Gly His His Arg
        1620                1625                1630

Arg Gln Val Ile Ala Ser Asp Leu Ile Ile Arg His Pro Tyr Ala Leu
    1635                1640                1645

Thr Leu Phe Glu Asp Ser Val Tyr Trp Thr Asp Arg Ala Thr Arg Arg
1650                1655                1660

Val Met Arg Ala Asn Lys Trp His Gly Gly Asn Gln Ser Val Val Met
1665                1670                1675                1680

Tyr Asn Ile Gln Trp Pro Leu Gly Ile Val Ala Val His Pro Ser Lys
            1685                1690                1695

Gln Pro Asn Ser Val Asn Pro Cys Ala Phe Ser Arg Cys Ser His Leu
        1700                1705                1710

Cys Leu Leu Ser Ser Gln Gly Pro His Phe Tyr Ser Cys Val Cys Pro
    1715                1720                1725

Ser Gly Trp Ser Leu Ser Pro Asp Leu Leu Asn Cys Leu Arg Asp Asp
    1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
            1765                1770                1775

Ile Gln Asn Gly Leu Asp Val Glu Phe Asp Ala Glu Gln Tyr Ile
        1780                1785                1790

Tyr Trp Val Glu Asn Pro Gly Glu Ile His Arg Val Lys Thr Asp Gly
            1795                1800                1805

Thr Asn Arg Thr Val Phe Ala Ser Ile Ser Met Val Gly Pro Ser Met
    1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
            1845                1850                1855
```

```
Arg Lys Thr Leu Ile Ala Asn Asp Gly Thr Ala Leu Gly Val Gly Phe
        1860                1865                1870

Pro Ile Gly Ile Thr Val Asp Pro Ala Arg Gly Lys Leu Tyr Trp Ser
    1875                1880                1885

Asp Gln Gly Thr Asp Ser Gly Val Pro Ala Lys Ile Ala Ser Ala Asn
        1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
            1925                1930                1935

Val Thr Gly Arg Gly Val Ile Glu Arg Gly Asn Val Asp Gly Thr Asp
        1940                1945                1950

Arg Met Ile Leu Val His Gln Leu Ser His Pro Trp Gly Ile Ala Val
        1955                1960                1965

His Asp Ser Phe Leu Tyr Tyr Thr Asp Glu Gln Tyr Glu Val Ile Glu
    1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Arg Asn Ala Ala
            2005                2010                2015

Glu Ser Ser Asn Gly Cys Ser Asn Asn Met Asn Ala Cys Gln Gln Ile
        2020                2025                2030

Cys Leu Pro Val Pro Gly Gly Leu Phe Ser Cys Ala Cys Ala Thr Gly
        2035                2040                2045

Phe Lys Leu Asn Pro Asp Asn Arg Ser Cys Ser Pro Tyr Asn Ser Phe
    2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
        2100                2105                2110

Asp Phe Ser Ser Ser Val Ala Ser Asp Asn Ala Ile Arg Arg Ile Lys
    2115                2120                2125

Pro Asp Gly Ser Ser Leu Met Asn Ile Val Thr His Gly Ile Gly Glu
    2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
            2165                2170                2175

Asn Thr Thr Tyr Arg Arg Val Leu Leu Lys Val Thr Val Asp Met Pro
        2180                2185                2190

Arg His Ile Val Val Asp Pro Lys Asn Arg Tyr Leu Phe Trp Ala Asp
        2195                2200                2205

Tyr Gly Gln Arg Pro Lys Ile Glu Arg Ser Phe Leu Asp Cys Thr Asn
    2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Asp Ser Leu Asp
            2245                2250                2255

Ile Ile Ala Arg Ile Arg Ile Asn Gly Glu Asn Ser Glu Val Ile Arg
        2260                2265                2270

Tyr Gly Ser Arg Tyr Pro Thr Pro Tyr Gly Ile Thr Val Phe Glu Asn
```

```
                2275              2280              2285
Ser Ile Ile Trp Val Asp Arg Asn Leu Lys Lys Ile Phe Gln Ala Ser
            2290              2295              2300
Lys Glu Pro Glu Asn Thr Glu Pro Pro Thr Val Ile Arg Asp Asn Ile
2305              2310              2315              2320
Asn Trp Leu Arg Asp Val Thr Ile Phe Asp Lys Gln Val Gln Pro Arg
                2325              2330              2335
Ser Pro Ala Glu Val Asn Asn Pro Cys Leu Glu Asn Asn Gly Gly
            2340              2345              2350
Cys Ser His Leu Cys Phe Ala Leu Pro Gly Leu His Thr Pro Lys Cys
                2355              2360              2365
Asp Cys Ala Phe Gly Thr Leu Gln Ser Asp Gly Lys Asn Cys Ala Ile
            2370              2375              2380
Ser Thr Glu Asn Phe Leu Ile Phe Ala Leu Ser Asn Ser Leu Arg Ser
2385              2390              2395              2400
Leu His Leu Asp Pro Glu Asn His Ser Pro Pro Phe Gln Thr Ile Asn
                2405              2410              2415
Val Glu Arg Thr Val Met Ser Leu Asp Tyr Asp Ser Val Ser Asp Arg
            2420              2425              2430
Ile Tyr Phe Thr Gln Asn Leu Ala Ser Gly Val Gly Gln Ile Ser Tyr
                2435              2440              2445
Ala Thr Leu Ser Ser Gly Ile His Thr Pro Thr Val Ile Ala Ser Gly
            2450              2455              2460
Ile Gly Thr Ala Asp Gly Ile Ala Phe Asp Trp Ile Thr Arg Arg Ile
2465              2470              2475              2480
Tyr Tyr Ser Asp Tyr Leu Asn Gln Met Ile Asn Ser Met Ala Glu Asp
                2485              2490              2495
Gly Ser Asn Arg Thr Val Ile Ala Arg Val Pro Lys Pro Arg Ala Ile
            2500              2505              2510
Val Leu Asp Pro Cys Gln Gly Tyr Leu Tyr Trp Ala Asp Trp Asp Thr
                2515              2520              2525
His Ala Lys Ile Glu Arg Ala Thr Leu Gly Gly Asn Phe Arg Val Pro
            2530              2535              2540
Ile Val Asn Ser Ser Leu Val Met Pro Ser Gly Leu Thr Leu Asp Tyr
2545              2550              2555              2560
Glu Glu Asp Leu Leu Tyr Trp Val Asp Ala Ser Leu Gln Arg Ile Glu
                2565              2570              2575
Arg Ser Thr Leu Thr Gly Val Asp Arg Glu Val Ile Val Asn Ala Ala
            2580              2585              2590
Val His Ala Phe Gly Leu Thr Leu Tyr Gly Gln Tyr Ile Tyr Trp Thr
                2595              2600              2605
Asp Leu Tyr Thr Gln Arg Ile Tyr Arg Ala Asn Lys Tyr Asp Gly Ser
            2610              2615              2620
Gly Gln Ile Ala Met Thr Thr Asn Leu Leu Ser Gln Pro Arg Gly Ile
2625              2630              2635              2640
Asn Thr Val Val Lys Asn Gln Lys Gln Cys Asn Asn Pro Cys Glu
                2645              2650              2655
Gln Phe Asn Gly Gly Cys Ser His Ile Cys Ala Pro Gly Pro Asn Gly
            2660              2665              2670
Ala Glu Cys Gln Cys Pro His Glu Gly Asn Trp Tyr Leu Ala Asn Asn
                2675              2680              2685
Arg Lys His Cys Ile Val Asp Asn Gly Glu Arg Cys Gly Ala Ser Ser
            2690              2695              2700
```

```
Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
            2725                2730                2735

Ala Leu His Thr Cys Ser Pro Thr Ala Phe Thr Cys Ala Asn Gly Arg
        2740                2745                2750

Cys Val Gln Tyr Ser Tyr Arg Cys Asp Tyr Tyr Asn Asp Cys Gly Asp
            2755                2760                2765

Gly Ser Asp Glu Ala Gly Cys Leu Phe Arg Asp Cys Asn Ala Thr Thr
        2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Thr Ser Asp Glu Lys Asn
            2805                2810                2815

Cys Pro Asp Arg Thr Cys Gln Ser Gly Tyr Thr Lys Cys His Asn Ser
            2820                2825                2830

Asn Ile Cys Ile Pro Arg Val Tyr Leu Cys Asp Gly Asp Asn Asp Cys
        2835                2840                2845

Gly Asp Asn Ser Asp Glu Asn Pro Thr Tyr Cys Thr Thr His Thr Cys
2850                2855                2860

Ser Ser Ser Glu Phe Gln Cys Ala Ser Gly Arg Cys Ile Pro Gln His
2865                2870                2875                2880

Trp Tyr Cys Asp Gln Glu Thr Asp Cys Phe Asp Ala Ser Asp Glu Pro
        2885                2890                2895

Ala Ser Cys Gly His Ser Glu Arg Thr Cys Leu Ala Asp Glu Phe Lys
        2900                2905                2910

Cys Asp Gly Gly Arg Cys Ile Pro Ser Glu Trp Ile Cys Asp Gly Asp
        2915                2920                2925

Asn Asp Cys Gly Asp Met Ser Asp Glu Asp Lys Arg His Gln Cys Gln
        2930                2935                2940

Asn Gln Asn Cys Ser Asp Ser Glu Phe Leu Cys Val Asn Asp Arg Pro
2945                2950                2955                2960

Pro Asp Arg Arg Cys Ile Pro Gln Ser Trp Val Cys Asp Gly Asp Val
            2965                2970                2975

Asp Cys Thr Asp Gly Tyr Asp Glu Asn Gln Asn Cys Thr Arg Arg Thr
        2980                2985                2990

Cys Ser Glu Asn Glu Phe Thr Cys Gly Tyr Gly Leu Cys Ile Pro Lys
        2995                3000                3005

Ile Phe Arg Cys Asp Arg His Asn Asp Cys Gly Asp Tyr Ser Asp Glu
        3010                3015                3020

Arg Gly Cys Leu Tyr Gln Thr Cys Gln Gln Asn Gln Phe Thr Cys Gln
3025                3030                3035                3040

Asn Gly Arg Cys Ile Ser Lys Thr Phe Val Cys Asp Glu Asp Asn Asp
            3045                3050                3055

Cys Gly Asp Gly Ser Asp Glu Leu Met His Leu Cys His Thr Pro Glu
            3060                3065                3070

Pro Thr Cys Pro Pro His Glu Phe Lys Cys Asp Asn Gly Arg Cys Ile
        3075                3080                3085

Glu Met Met Lys Leu Cys Asn His Leu Asp Asp Cys Leu Asp Asn Ser
3090                3095                3100

Asp Glu Lys Gly Cys Gly Ile Asn Glu Cys His Asp Pro Ser Ile Ser
3105                3110                3115                3120

Gly Cys Asp His Asn Cys Thr Asp Thr Leu Thr Ser Phe Tyr Cys Ser
        3125                3130                3135
```

-continued

Cys Arg Pro Gly Tyr Lys Leu Met Ser Asp Lys Arg Thr Cys Val Asp
            3140                3145                3150

Ile Asp Glu Cys Thr Glu Met Pro Phe Val Cys Ser Gln Lys Cys Glu
        3155                3160                3165

Asn Val Ile Gly Ser Tyr Ile Cys Lys Cys Ala Pro Gly Tyr Leu Arg
    3170                3175                3180

Glu Pro Asp Gly Lys Thr Cys Arg Gln Asn Ser Asn Ile Glu Pro Tyr
3185                3190                3195                3200

Leu Ile Phe Ser Asn Arg Tyr Tyr Leu Arg Asn Leu Thr Ile Asp Gly
            3205                3210                3215

Tyr Phe Tyr Ser Leu Ile Leu Glu Gly Leu Asp Asn Val Val Ala Leu
        3220                3225                3230

Asp Phe Asp Arg Val Glu Lys Arg Leu Tyr Trp Ile Asp Thr Gln Arg
    3235                3240                3245

Gln Val Ile Glu Arg Met Phe Leu Asn Lys Thr Asn Lys Glu Thr Ile
3250                3255                3260

Ile Asn His Arg Leu Pro Ala Ala Glu Ser Leu Ala Val Asp Trp Val
3265            3270                3275                3280

Ser Arg Lys Leu Tyr Trp Leu Asp Ala Arg Leu Asp Gly Leu Phe Val
        3285                3290                3295

Ser Asp Leu Asn Gly Gly His Arg Arg Met Leu Ala Gln His Cys Val
    3300                3305                3310

Asp Ala Asn Asn Thr Phe Cys Phe Asp Asn Pro Arg Gly Leu Ala Leu
        3315                3320                3325

His Pro Gln Tyr Gly Tyr Leu Tyr Trp Ala Asp Trp Gly His Arg Ala
    3330                3335                3340

Tyr Ile Gly Arg Val Gly Met Asp Gly Thr Asn Lys Ser Val Ile Ile
3345                3350                3355                3360

Ser Thr Lys Leu Glu Trp Pro Asn Gly Ile Thr Ile Asp Tyr Thr Asn
            3365                3370                3375

Asp Leu Leu Tyr Trp Ala Asp Ala His Leu Gly Tyr Ile Glu Tyr Ser
        3380                3385                3390

Asp Leu Glu Gly His His Arg His Thr Val Tyr Asp Gly Ala Leu Pro
    3395                3400                3405

His Pro Phe Ala Ile Thr Ile Phe Glu Asp Thr Ile Tyr Trp Thr Asp
    3410                3415                3420

Trp Asn Thr Arg Thr Val Glu Lys Gly Asn Lys Tyr Asp Gly Ser Asn
3425                3430                3435                3440

Arg Gln Thr Leu Val Asn Thr Thr His Arg Pro Phe Asp Ile His Val
            3445                3450                3455

Tyr His Pro Tyr Arg Gln Pro Ile Val Ser Asn Pro Cys Gly Thr Asn
        3460                3465                3470

Asn Gly Gly Cys Ser His Leu Cys Leu Ile Lys Pro Gly Gly Lys Gly
    3475                3480                3485

Phe Thr Cys Glu Cys Pro Asp Asp Phe Arg Thr Leu Gln Leu Ser Gly
    3490                3495                3500

Ser Thr Tyr Cys Met Pro Met Cys Ser Ser Thr Gln Phe Leu Cys Ala
3505                3510                3515                3520

Asn Asn Glu Lys Cys Ile Pro Ile Trp Trp Lys Cys Asp Gly Gln Lys
            3525                3530                3535

Asp Cys Ser Asp Gly Ser Asp Glu Leu Ala Leu Cys Pro Gln Arg Phe
        3540                3545                3550

Cys Arg Leu Gly Gln Phe Gln Cys Ser Asp Gly Asn Cys Thr Ser Pro

```
                  3555                3560                3565
Gln Thr Leu Cys Asn Ala His Gln Asn Cys Pro Asp Gly Ser Asp Glu
        3570                3575                3580

Asp Arg Leu Leu Cys Glu Asn His His Cys Asp Ser Asn Glu Trp Gln
3585                3590                3595                3600

Cys Ala Asn Lys Arg Cys Ile Pro Glu Ser Trp Gln Cys Asp Thr Phe
            3605                3610                3615

Asn Asp Cys Glu Asp Asn Ser Asp Glu Asp Ser Ser His Cys Ala Ser
        3620                3625                3630

Arg Thr Cys Arg Pro Gly Gln Phe Arg Cys Ala Asn Gly Arg Cys Ile
            3635                3640                3645

Pro Gln Ala Trp Lys Cys Asp Val Asp Asn Asp Cys Gly Asp His Ser
        3650                3655                3660

Asp Glu Pro Ile Glu Glu Cys Met Ser Ser Ala His Leu Cys Asp Asn
3665                3670                3675                3680

Phe Thr Glu Phe Ser Cys Lys Thr Asn Tyr Arg Cys Ile Pro Lys Trp
            3685                3690                3695

Ala Val Cys Asn Gly Val Asp Asp Cys Arg Asp Asn Ser Asp Glu Gln
        3700                3705                3710

Gly Cys Glu Glu Arg Thr Cys His Pro Val Gly Asp Phe Arg Cys Lys
            3715                3720                3725

Asn His His Cys Ile Pro Leu Arg Trp Gln Cys Asp Gly Gln Asn Asp
        3730                3735                3740

Cys Gly Asp Asn Ser Asp Glu Glu Asn Cys Ala Pro Arg Glu Cys Thr
3745                3750                3755                3760

Glu Ser Glu Phe Arg Cys Val Asn Gln Gln Cys Ile Pro Ser Arg Trp
            3765                3770                3775

Ile Cys Asp His Tyr Asn Asp Cys Gly Asp Asn Ser Asp Glu Arg Asp
        3780                3785                3790

Cys Glu Met Arg Thr Cys His Pro Glu Tyr Phe Gln Cys Thr Ser Gly
            3795                3800                3805

His Cys Val His Ser Glu Leu Lys Cys Asp Gly Ser Ala Asp Cys Leu
        3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Cys Gly Asp Gly Ser Asp Glu
        3860                3865                3870

Glu Leu His Leu Cys Leu Asp Val Pro Cys Asn Ser Pro Asn Arg
        3875                3880                3885

Phe Arg Cys Asp Asn Asn Arg Cys Ile Tyr Ser His Glu Val Cys Asn
        3890                3895                3900

Gly Val Asp Asp Cys Gly Asp Gly Thr Asp Glu Thr Glu Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Asp Ala Asp Asp
        3940                3945                3950

Cys Gly Asp Trp Ser Asp Glu Leu Gly Cys Asn Lys Gly Lys Glu Arg
            3955                3960                3965

Thr Cys Ala Glu Asn Ile Cys Glu Gln Asn Cys Thr Gln Leu Asn Glu
        3970                3975                3980
```

```
Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
        4020                4025                4030

Ala Asp Gly Phe Thr Ser Met Ser Asp Arg Pro Gly Lys Arg Cys Ala
            4035                4040                4045

Ala Glu Gly Ser Ser Pro Leu Leu Leu Leu Pro Asp Asn Val Arg Ile
4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Lys Asp Ile
            4085                4090                4095

Gly Leu Ser Val Val Tyr Tyr Thr Val Arg Gly Glu Gly Ser Arg Phe
            4100                4105                4110

Gly Ala Ile Lys Arg Ala Tyr Ile Pro Asn Phe Glu Ser Gly Arg Asn
            4115                4120                4125

Asn Leu Val Gln Glu Val Asp Leu Lys Leu Lys Tyr Val Met Gln Pro
4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
            4165                4170                4175

Lys Trp Leu Ile Ser Thr Asp Leu Asp Gln Pro Ala Ala Ile Ala Val
            4180                4185                4190

Asn Pro Lys Leu Gly Leu Met Phe Trp Thr Asp Trp Gly Lys Glu Pro
            4195                4200                4205

Lys Ile Glu Ser Ala Trp Met Asn Gly Glu Asp Arg Asn Ile Leu Val
            4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
            4245                4250                4255

Ile Lys Tyr Asp Gly Thr Asp Arg Arg Val Ile Ala Lys Glu Ala Met
            4260                4265                4270

Asn Pro Tyr Ser Leu Asp Ile Phe Glu Asp Gln Leu Tyr Trp Ile Ser
            4275                4280                4285

Lys Glu Lys Gly Glu Val Trp Lys Gln Asn Lys Phe Gly Gln Gly Lys
            4290                4295                4300

Lys Glu Lys Thr Leu Val Val Asn Pro Trp Leu Thr Gln Val Arg Ile
4305                4310                4315                4320

Phe His Gln Leu Arg Tyr Asn Lys Ser Val Pro Asn Leu Cys Lys Gln
                4325                4330                4335

Ile Cys Ser His Leu Cys Leu Leu Arg Pro Gly Gly Tyr Ser Cys Ala
            4340                4345                4350

Cys Pro Gln Gly Ser Ser Phe Ile Glu Gly Ser Thr Thr Glu Cys Asp
            4355                4360                4365

Ala Ala Ile Glu Leu Pro Ile Asn Leu Pro Pro Cys Arg Cys Met
            4370                4375                4380

His Gly Gly Asn Cys Tyr Phe Asp Glu Thr Asp Leu Pro Lys Cys Lys
4385                4390                4395                4400

Cys Pro Ser Gly Tyr Thr Gly Lys Tyr Cys Glu Met Ala Phe Ser Lys
            4405                4410                4415
```

-continued

```
Gly Ile Ser Pro Gly Thr Thr Ala Val Ala Val Leu Leu Thr Ile Leu
            4420            4425            4430

Leu Ile Val Val Ile Gly Ala Leu Ala Ile Ala Gly Phe Phe His Tyr
        4435            4440            4445

Arg Arg Thr Gly Ser Leu Leu Pro Ala Leu Pro Lys Leu Pro Ser Leu
    4450            4455            4460

Ser Ser Leu Val Lys Pro Ser Glu Asn Gly Asn Gly Val Thr Phe Arg
4465            4470            4475            4480

Ser Gly Ala Asp Leu Asn Met Asp Ile Gly Val Ser Gly Phe Gly Pro
                4485            4490            4495

Glu Thr Ala Ile Asp Arg Ser Met Ala Met Ser Glu Asp Phe Val Met
            4500            4505            4510

Glu Met Gly Lys Gln Pro Ile Ile Phe Glu Asn Pro Met Tyr Ser Ala
            4515            4520            4525

Arg Asp Ser Ala Val Lys Val Val Gln Pro Ile Gln Val Thr Val Ser
    4530            4535            4540

Glu Asn Val Asp Asn Lys Asn Tyr Gly Ser Pro Ile Asn Pro Ser Glu
4545            4550            4555            4560

Ile Val Pro Glu Thr Asn Pro Thr Ser Pro Ala Ala Asp Gly Thr Gln
                4565            4570            4575

Val Thr Lys Trp Asn Leu Phe Lys Arg Lys Ser Lys Gln Thr Thr Asn
            4580            4585            4590

Phe Glu Asn Pro Ile Tyr Ala Gln Met Glu Asn Glu Gln Lys Glu Ser
            4595            4600            4605

Val Ala Ala Thr Pro Pro Pro Ser Pro Ser Leu Pro Ala Lys Pro Lys
    4610            4615            4620

Pro Pro Ser Arg Arg Asp Pro Thr Pro Thr Tyr Ser Ala Thr Glu Asp
4625            4630            4635            4640

Thr Phe Lys Asp Thr Ala Asn Leu Val Lys Glu Asp Ser Glu Val
                4645            4650            4655
```

USE OF MEGALIN IN URINE AS MARKER FOR DETECTING RENAL DISORDER

CROSS-REFERENCE TO RELATED APPLICATIONS

This application is the U.S. national phase of PCT/JP2010/057490, filed Apr. 27, 2010, which claims priority from Japanese patent application No. 2009-108493, filed Apr. 27, 2009. The entire subject matter of each of these applications is incorporated by reference.

The present invention was the subject of one or more joint research agreements executed between Denka Seiken Co. Ltd. and Niigata University and Juntendo University School of Medicine, a division of Juntendo Educational Foundation.

TECHNICAL FIELD

The present invention relates to a detection kit and a detection marker used for detecting a renal disease. Also, the present invention relates to a method for detecting a pathological condition using the megalin level in urine as an indicator for detecting a renal disorder in the form of a marker. In addition, the present invention relates to a method for evaluating effects of treating a renal disease.

BACKGROUND OF THE INVENTION

Megalin is a glycoprotein expressed in the renal proximal tubular epithelial cells with a molecular weight of approximately 600 kDa, It is also known as the glycoprotein 330 (gp330) or low-density lipoprotein (LDL)-receptor related protein 2 (LRP2). (Non-Patent Documents 1 and 2).

Megalin serves as an endocytic receptor associated with endocytosis/resorption of a protein or the like in the proximal tubular lumen in the kidney before urinary excretion. A ligand of a resorbed protein or the like is then degraded by a lysosome in the proximal tubular epithelial cells (Non-Patent Document 3).

Clinically, a patient with diabetic nephropathy is first afflicted with diabetes, and the patient then develops microalbuminuria, which leads to continued proteinuria and then to terminal renal failure. Research that points out the significance of glomerular hyperfiltration and microalbuminuria as clinical pictures appearing in an early stage of nephropathy is featured. Specifically, it has been known that patients with type I diabetes exhibit increases in renal blood flow and glomerular filtration rate at the early phase of the disease, development of microalbuminuria was then pointed out as an early-phase change resulting in the future development of nephropathy, and the concept of early stage of nephropathy was proposed. In addition, it was discovered that the amount of albumin excreted into the urine increased to abnormal levels in this stage, although it did not lead to development of proteinuria. Thus, such symptom was designated as "microalbuminuria" (Non-Patent Document 4).

Thereafter, the clinical significance of "microalbumin" was established by Mogensen C. E., Viberti G. C. et al., and the presence of microalbuminuria is strongly correlated with the later progression of nephropathy. Thus, microalbumin is used for clinical diagnosis nowadays. It has been reported that microalbuminuria is caused by the equilibrium and failure in functions in glomerular filtration and tubular resorption (Non-Patent Documents 5, 6, 7, 8, 9, and 10).

It has also been reported that tubular albumin resorption is caused by megalin-mediated endocytosis (Non-Patent Documents 11, 12, 13, 14, 15, 16, 17, 18, and 19).

When a renal disorder advances from microalbuminuria, continued proteinuria (i.e., overt proteinuria) develops. In this stage, positive results for proteinuria are continuously found with the use of a paper test, and the disease becomes detectable with medical checkups at this stage.

According to the report of Araki S. et al., the results of a six-year follow-up study of treatment of 216 early stage of nephropathy cases demonstrated that 51% cases exhibited remission of nephropathy (i.e., improved to normal albuminuria), which occurred with higher frequency than progression (i.e., progression to overt nephropathy, 28%) (Non-Patent Document 22).

As a result of the analysis, four factors associated with remission have been exemplified: (i) a short duration following the development of microalbuminuria; (ii) use of a renin-angiotensin system inhibitor; (iii) low systolic blood pressure; and (iv) sufficient blood sugar control. Specifically, earlier diagnosis, recognition of pathological conditions, and therapeutic management of renal disorders are considered to be important to prevent advancement of diabetic nephropathy. Basic treatment methods for diabetic nephropathy are (1) blood sugar control, (2) blood pressure control, (3) suppression of the renin-angiotensin system, (4) lipid control, (5) alimentary therapy (restriction of salt and protein intake), and (6) improvement in lifestyle habits, such as smoking abstinence. In order to inhibit the development and progression of nephropathy, precise and active treatment based on evidence attained by clinical studies is necessary. Regarding blood sugar control, evidence has been attained by DCCT, UKPDS, and the Kumamoto study, which have been important for the prevention of nephropathy progression. Regarding the importance of blood pressure control, much evidence has been accumulated, including on ACE inhibitors and ARB.

Among chronic glomerulonephritis symptoms, in contrast, glomerular mesangial cell proliferation, mesangium matrix enlargement (hyperplasia), and granular deposits (mainly IgA) in the mesangial region are observed in the case of IgA nephropathy. Diagnosis of IgA nephropathy is confirmed by renal biopsy. IgA nephropathy is often detected based on asymptomatic urinary abnormalities. Continuous microscopic hematuria is inevitable, and intermittent or continuous proteinuria and macroscopic hematuria are occasionally observed. Macroscopic hematuria often occurs with acute upper respiratory tract infection. Diagnosis of urinary abnormality requires at least three instances of urine analysis, and at least two of these instances involve microscopic visualization of urinary sediments, which are conducted in addition to general qualitative urine analysis. High serum IgA levels of 315 mg/dl or higher are observed in half of the patients. A mild asymptomatic urinary abnormality should not be depreciated. Laboratory findings on IgA nephropathy are useful for the evaluation of activity and progression of renal disorders. Only hematuria is observed at an early stage, and proteinuria develops along with the progression of disease stages. Examples of unfavorable factors include high blood pressure, continuation of mild- to high-proteinuria, and renal dysfunction observed at the first medical examination. Thus, comprehensive evaluation of various laboratory findings and adequate treatment in accordance with activity of glomerulonephritis and renal disorder progression are necessary. Since IgA nephropathy is often detected by chance proteinuria/hematuria, differential diagnosis of hematuria is first required. Renal biopsy is then performed as a definite diagnosis. There are contraindications involved in renal biopsy, and there are many restrictions. In actual clinical settings, renal biopsy cannot be performed in many cases, and, at present, there is no solid, accurate indication of whether or not renal biopsy should be carried out. In renal biopsy for definite diagnosis, glomerulosclerosis symptoms from the focal and the segmental to the diffuse and the global (spherical) are evaluated with the use of mesangial proliferative changes as indicators in light microscopic findings, and diffuse glomerulosclerosis symptoms are evaluated with the use of granular IgA deposition mainly in the mesangial region as an indicator for the fluorescence antibody method or enzyme antibody method (i.e., IgA is dominant to other immunoglobulins). Evaluation is made with the deposition of electron-dense substances within the mesangial matrix (centered on a paramesangial region, in particular) as an indicator for electron microscopic findings. Prognosis based on renal biopsy is determined based on histological findings from light microscope images of renal biopsy samples, and patients are divided into the following four groups.

1) Good Prognosis Group: The Group with Little Likelihood of Progression to Dialysis Therapy Glomerular findings: Mild mesangial cell proliferation and increased matrix are observed. No glomerulosclerosis, crescent formation, or adhesion to Bowman's capsule are observed.

Tubular, interstitial, and vascular findings: No prominent changes are observed in the renal tubule, the interstitium, or the blood vessels.

2) Relatively Good Prognosis Group: The Group with Less Likelihood of Progression to Dialysis Therapy Glomerular findings: Mild mesangial cell proliferation and increased matrix are observed. Glomerulosclerosis, crescent formation, and adhesion to Bowman's capsule are observed in less than 10% of the biopsy glomeruli.

Tubular, interstitial, and vascular findings: No prominent changes are observed in the renal tubule, the interstitium, or the blood vessels.

3) Relatively Poor Prognosis Group: The Group with Likelihood of Transition to Dialysis Therapy in 5 to 20 Years Glomerular findings: Moderate mesangial cell proliferation and increased matrix are observed. Glomerulosclerosis, crescent formation, and adhesion to Bowman's capsule are observed in 10% to 30% of the biopsy glomeruli.

Tubular, interstitial, and vascular findings: Slight tubular atrophy, slight cellular infiltration in the interstitium except for around some sclerosed glomeruli, and mild vascular sclerosis are observed in the blood vessels.

4) Poor Prognosis Group: The Group with likelihood of Transition to Dialysis Therapy within 5 Years Glomerular findings: Severe mesangial cell proliferation and increased matrix are observed. Glomerulosclerosis, crescent formation, and adhesion to Bowman's capsule are observed in 30% or more of the biopsy glomeruli. When the sites of sclerosis are totalled and converted to the global sclerosis, further, the rate of glomerulosclerosis is 50% or higher. Compensatory glomerular hypertrophy is occasionally observed.

Tubular, interstitial, and vascular findings: Severe tubular atrophy, interstitial cellular infiltration, and fibrosis are observed. Hyperplasia or degeneration is occasionally observed on some renal arteriolar walls.

The basis of medication for IgA nephropathy is selection of a drug suitable for the pathological conditions of each patient. Adrenal cortical steroid therapy is suitable for a case with a creatinine clearance (Ccr) of 70 ml/min or higher, urinary protein of 1 to 2 g/day, and the acute inflammation symptoms detected by the renal biopsy as major symptoms. In contrast, drug therapy involving the use of inhibitors of the renin-angiotensin system or fish oil is selected for cases mainly involving chronic lesions and exhibiting slow progression. Renal functions of patients in the poor prognosis group exhibiting moderate or severe renal dysfunction and mainly involving chronic sclerosing lesion cannot be maintained only by steroid therapy for a long period of time, and development of effective therapeutic techniques capable of improving the prognosis of renal functions has been awaited. In addition, use of anti-platelet agents, anticoagulant therapy, Kuremejin therapy, tonsillectomy therapy, or the like is occasionally employed. IgA nephropathy occurs at a young age, and 30% to 40% of patients develop terminal renal failure. Economic and social burdens are serious when a patient has to start dialysis treatment at a young age. As described above, there are no accurate and precise indicators for differential diagnosis or diagnosis enabling prognostic prediction of IgA nephropathy at present.

The number of patients with terminal renal failure who are in need of dialysis is increasing all over the world, and it is a serious issue of concern in terms of medical economy. Prediction and diagnosis of pathological conditions of renal disorders and, in particular, diabetic nephropathy or IgA nephropathy, are most critical in order to provide adequate treatment. However, accuracy of conventional diagnostic techniques is insufficient for prognostic prediction or diagnosis of the degree of disorder.

In the preceding stage of diabetic nephropathy, microalbuminuria is not observed in urine, and nephropathy cannot be detected based on current clinical findings. Minimal albuminuria is deduced to occur at the early stage of nephropathy. Even if renal functions are normal or sometimes accelerated, nodular lesions may be present in glomeruli at this stage. Thus, whether or not microalbuminuria is useful as an indicator for early diagnosis of diabetic nephropathy remains problematic. In recent years, a case of rapidly progressive renal disorder directly leading to renal failure (stage-IV diabetic nephropathy) without the overt albuminuria stage (stage-III diabetic nephropathy (the overt nephropathy stage)) was found in the groups of diabetic nephropathy patients exhibiting microalbuminuria (stage-II diabetic nephropathy: early stage of nephropathy). Thus, the possible problematic nature of the clinical significance of the use of albuminuria for prognostic prediction of a renal disease and for precise and early diagnosis of the degree of disorder (progression in pathological conditions) as an indicator has been discussed (Perkins B. A., Krolewski A. S. et al., 2007, J. Am. Soc. Nephrol. 18 (4), 1353-1361; de Boer I. H., Steffes M. W., 2007, J. Am. Soc. Nephrol. 18 (4), 1036-1037).

IgA nephropathy prognosis is histologically classified based on renal biopsy findings, and the results are used for prognostic prediction and determination of the course of treatment. However, there are some restrictions on renal biopsy, and application of renal biopsy is restricted to the following cases: i) 1.0 g or more protein in urine is observed per day; ii) although a renal disorder of unknown etiology is observed, renal atrophy is not observed via an imaging test; iii) chronic glomerulonephritis with continuous and progressive hematuria is suspected; and iv) renal functions are rapidly lowered. Meanwhile, contraindications to renal biopsy are as follows: i) renal atrophy has already been observed via the imaging test due to chronic renal dysfunctions; ii) it is difficult to arrest hemorrhage due to bleeding tendency or uncontrollable high blood pressure; iii) a patient has a polycystic kidney; and iv) the patient cannot keep quiet or follow instructions during renal biopsy or during and after testing. In actual clinical settings, renal biopsy cannot be performed in many cases, and there are no accurate and definitive indicators for the determination of whether or not renal biopsy should be performed at present.

In addition to chronic renal disorders represented by diabetic nephropathy and IgA nephropathy described above, acute kidney injury (AKI) has drawn attention and become an issue of concern. Regarding AKI, functional abnormalities in renal hemodynamics have been regarded as critical, in addition to structural abnormalities (i.e., acute tubular necrosis) in recent years.

The term "acute renal failure" refers to a condition in which renal functions are rapidly lowered, and many acute renal failure cases are characterized by lowered renal functions caused by tubular necrosis. Causes of acute renal failure include prerenal renal failure, intrinsic renal failure, and postrenal renal failure. Prerenal renal failure occurs when the kidney is exposed to ischaemia by a lowered extracellular fluid volume due to bleeding from injury, dehydration, vomition, and diarrhea, decreased effective circulating blood volume due to cardiogenic shock, and decreased renal blood flow due to dissecting aneurysm of aorta or renal arterial thrombosis. Intrinsic renal failure is a disorder directly imposed on the renal tissue, such as in glomerular diseases (e.g., acute glomerulonephritis, rapidly progressive glomerulonephritis, and polyarteritis nodosa), acute tubular necrosis (caused by the use of an aminoglycoside antibiotics, an anti-inflammatory and analgesic agent, an anti-tumor agent, or contrast medium), or acute interstitial glomerulonephritis (caused by the use of a β-lactam antibiotics, an anti-inflammatory or analgesic agent, or an anticonvulsant). In the case of postrenal renal failure, the urine flow is obstructed and urinary excretion is prevented by ureteral obstruction (ureteral calculus), vesical and urethral obstruction (prostate hypertrophy and prostate cancer), or pelvic tumors.

Many acute renal injuries require ICU controls after cardiotomy and aorta replacement surgery, and recognition of pathological conditions is required on an hourly basis after disease development. At present, improvement in the vital prognosis for acute renal failure cannot be expected without early diagnosis and immediate intervention.

At present, acute renal failure is generally diagnosed based on serum creatinine and urine levels; however, diagnosis based on these two items suffers from a problem. That is, no diagnostic standards have been established for these two items, and there have been 35 different definitions of acute renal failure. In order to solve this problem, the acute renal failure network was established as a global effort, and diagnostic standards for acute renal failure were proposed. According to these diagnostic standards, a person is diagnosed as having acute renal failure when (1) the serum creatinine level is increased by 1.5 times or more or 0.3 mg/dl or more and (2) hypouresis of 0.5 ml/kg/hour continues for 6 hours or longer. As with the case of chronic renal disease stage classification, acute renal failure stage classification is proposed in particular (e.g., RIFLE or AKIN classification).

However, diagnosis based on the two items described above still suffers from problems. The serum creatinine level is not elevated immediately when the glomerular filtration rate is lowered due to a renal disorder. The serum creatinine level occasionally continues to increase for a while even when the glomerular filtration rate is in a recovery trend. Thus, usefulness of serum creatinine level as an early marker for monitoring acute changes or a marker for monitoring of therapeutic effects or prognostic prediction cannot be said to be satisfactory. In addition, serum creatinine level is likely to be influenced by extrarenal factors, such as body weight, race, sexuality, drugs, muscle metabolism, or nutritional conditions. Since diagnosis based on urine level takes a long time, also, it is not suitable as a marker for acute renal failure, which requires recognition of pathological conditions on an hourly basis after disease development. Therefore, development of a biomarker, which enables easy measurement, is less likely to be influenced by other biological factors, and enables early detection, risk classification, and prognostic prediction of a disease is an urgent need.

PRIOR ART DOCUMENTS

[Patent Document]
Patent Document 1: WO 2007/119563
[Non-Patent Documents]
Non-Patent Document 1: Christensen E. I., Willnow T. E., 1999, J. Am. Soc. Nephrol. 10, 2224-2236
Non-Patent Document 2: Zheng G, McCluskey R. T. et al., 1994, J. Histochem. Cytochem. 42, 531-542
Non-Patent Document 3: Mausbach A. B., Christensen E. I., 1992, Handbook of physiology: Renal Physiology, Windhager, editor, New York, Oxford University Press, 42-207
Non-Patent Document 4: Keen H., Chlouverakis C., 1963, Lancet II, 913-916
Non-Patent Document 5: Tojo A., Endou H. et al., 2001, Histochem. Cell. Biol. 116 (3), 269-276
Non-Patent Document 6: Tucker B. J., Blantz R. C. et al., 1993, J. Clin. Invest. 92 (2), 686-694
Non-Patent Document 7: Evangelista C., Capasso G. et al., 2006, G. Ital. Nefrol. 34, S16-20
Non-Patent Document 8: Pollock C. A., Poronnik P., 2007, Curr. Opin. Nephrol. Hypertens. 16 (4), 359-364
Non-Patent Document 9: Rippe C., Rippe B. et al., 2007, Am. J. Physiol. Renal. Physiol. 293 (5), F1533-1538
Non-Patent Document 10: Blanz R. C., Thomson S. C. et al., 2007, Trans. Am. Clin. Climatol. Assoc. 118, 23-43
Non-Patent Document 11: Hosojima M., Saito A. et al., 2008, Endocriology, 16
Non-Patent Document 12: Baines R. J., Brunskill N. J., 2008, Nephron. Exp. Nephrol. 110 (2), e67-71
Non-Patent Document 13: Motoyoshi Y., Ichikawa I. et al., 2008, Kidney. Int. 74 (10), 1262-1269
Non-Patent Document 14: Vegt E., Boerman O. C. et al., 2008, J. Nucl. Med. 49 (9), 1506-1511
Non-Patent Document 15: Haraldsson B., Deen W. M. et al., 2008, 88 (2), 451-487
Non-Patent Document 16: Odera K., Takahashi R. et al., 2007, 8 (5), 505-515
Non-Patent Document 17: Brunskill N., 2001, Am. J. Kidney. Dis. 37, S17-20
Non-Patent Document 18: Cui S., Christensen E. I. et al., 1996, Am. J. Physiol. 271, F900-7
Non-Patent Document 19: Saito A., Gejyo F. et al., 2005, Ann. N. Y. Acad. Sci. 1043, 637-643
Non-Patent Document 20: Perkins B. A., Krolewski A. S. et al., 2007, J. Am. Soc. Nephrol. 18 (4), 1353-1361
Non-Patent Document 21: de Boer I. H., Steffes M. W., 2007, J. Am. Soc. Nephrol. 18 (4), 1036-1037
Non-Patent Document 22: Araki S., Sugimoto T. et al., 2005, Diabetes. 54, 2983-2987
Non-Patent Document 23: Tojo A., Fujita T. et al., 2003, Hypertens. Res. 26 (5), 413-419

DISCLOSURE OF THE INVENTION

The present invention is intended to provide a marker for detecting a renal disorder, such as diabetic nephropathy or IgA nephropathy, and a method for detecting a renal disorder using such marker.

As described above, development of a novel detection marker used for prognostic prediction of a renal disorder and for accurate and early judgment of the degree of disorder (i.e., the progression of pathological conditions) and a method for detecting a renal disorder using such marker at an early stage has been awaited. However, there were no such markers or detection methods in the past. Such a marker enables prognostic prediction of a renal disorder and accurate and early judgment of the degree of disorder (i.e., the progression of pathological conditions), and such a marker also enables preventive care aimed at inhibition of development and progression of progressive renal disorder.

The present inventors have conducted concentrated studies in order to develop a novel marker used for prognostic prediction of a renal disorder and accurate and early judgment of the degree of disorder (i.e., the progression of pathological conditions). As a result, they discovered a biomarker referred to as "megalin" that appears in the urine as pathological conditions worsen in diabetic nephropathy, which exhibits a high incidence of poor prognosis, and in particular, in progressive renal disorders such as type II diabetic nephropathy or IgA nephropathy. Specifically, they discovered that the amount of megalin excreted into the urine of a patient with a progressive renal disorder, such as diabetic nephropathy and, in particular, type II diabetic nephropathy or IgA nephropathy, was higher than that of a healthy individual, and thus was useful as a marker for prognostic prediction of a renal disorder or diagnosis of the degree of disorder (i.e., the progression of pathological conditions). In addition, the present inventors developed a detection kit for detecting renal disorders, and, in particular, diabetic nephropathy and IgA nephropathy, with the use of megalin as a marker. When using such kit, a urine sample is collected, the human megalin level in the urine is quantitatively measured with the use of a detection reagent, and the determined urinary excretion level is used as an indicator for prognostic prediction of a renal disorder or diagnosis of the degree of disorder (i.e., the progression of pathological conditions). With the use of this diagnostic kit, pathological conditions of a renal disorder can be recognized. Prognostic prediction of a renal disorder, and, in particular, diabetic nephropathy or IgA nephropathy, or diagnosis of the degree of disorder (i.e., the progression of pathological conditions) was difficult in the past. However, the diagnostic kit of the present invention enables prediction or monitoring of therapeutic effects and provision of more effective therapeutic methods.

Specifically, the present invention is as follows.

[1] Use of human megalin in a urine sample obtained from a subject as a diagnostic marker for detecting a renal disorder.

[2] The use of human megalin in urine according to [1], wherein the renal disorder is detected for prognostic prediction.

[3] The use of human megalin in urine according to [2], wherein the prognostic prediction of a renal disorder is performed to evaluate tubular dysfunctions.

[4] The use of human megalin in urine according to [1], wherein the renal disorder is detected to evaluate the degree of disorder.

[5] The use of human megalin in urine according to [4], wherein the degree of renal disorder is evaluated to evaluate tubular dysfunctions.

[6] The use of human megalin in urine according to any of [1] to [5], wherein the renal disorder is selected from the group consisting of diabetic nephropathy, IgA nephropathy, nephrotic syndrome, chronic glomerulonephritis, membranous nephropathy, ANCA-associated glomerulonephritis, systemic erythematodes (lupus glomerulonephritis), Henoch-Schönlein purpura nephritis, interstitial glomerulonephritis, crescentic glomerulonephritis, focal glomerulosclerosis, nephrosclerosis, acute renal failure, chronic renal failure, renal amyloidosis, scleroderma renal crisis, interstitial glomerulonephritis caused by Sjogren's syndrome, and drug nephropathy.

[7] The use of human megalin in urine according to any of [1] to [5], wherein the renal disorder is diabetic nephropathy.

[8] The use of human megalin in urine according to any of [1] to [5], wherein the renal disorder is IgA nephropathy.

[9] The use of human megalin in urine according to any of [1] to [5], wherein the renal disorder is acute renal failure.

This description includes part or all of the contents as disclosed in the description and/or drawings of Japanese Patent Application No. 2009-108493, which is a priority document of the present application.

PREFERRED EMBODIMENTS OF THE INVENTION

Figure 1:
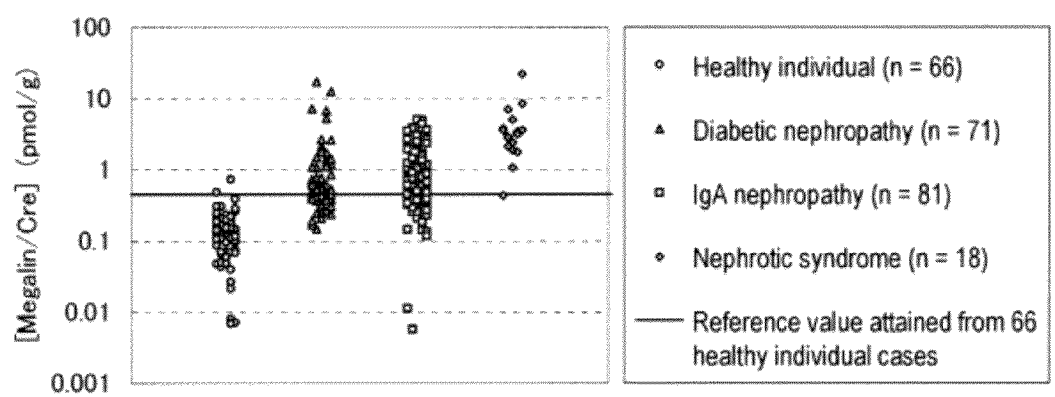
FIG. 1 shows the results of measurement of the amount of human megalin excreted into the urine (creatinine correction value) in cases of type II diabetic nephropathy (71 cases), IgA nephropathy (81 cases), and nephrotic syndrome (18 cases).

Hereafter, the present invention is described in detail.

The present invention involves the use of human megalin in a urine specimen as a marker for a renal disorder. SEQ ID NO: 1 shows the nucleotide sequence of human megalin and SEQ ID NO: 2 shows the amino acid sequence of human megalin. Human megalin in urine may be measured by any technique. For example, a ligand capable of binding to human megalin may be used.

According to an embodiment, two ligands capable of binding to human megalin are used, the first ligand is bound to a solid support, and the second ligand is labeled and used.

Any solid supports that are used in conventional immunoanalytical techniques can be used. For example, wells of a plastic microtiter plate or magnetic particles can be preferably used. An example of a ligand capable of binding to human megalin is an anti-human megalin antibody, and a monoclonal or polyclonal antibody can be used. Lectin, which is specific to a sugar chain of human megalin, can be used as a ligand capable of binding to human megalin. Examples of lectin include, but are not limited to, concanavalin A, wheat germ agglutinin (WGA), *Ricinus communis* lectin (RCA), and *Lens culinaris* lectin (LCA). Further examples of ligands capable of binding to human megalin include substances selected from the following group of substances or fragments capable of binding thereto: vitamin-binding proteins, such as transcobalamin-vitamin $B_{12}$, vitamin-D-binding protein, and retinol-binding protein; lipoproteins, such as apolipoprotein B, apolipoprotein E, apolipoprotein J/clusterin, and apolipoprotein H; hormones and hormone receptors, such as parathyroid hormone (PTH), insulin, epidermal growth factor (EGF), prolactin, leptin, and thyroglobulin, and receptors thereof; immune and stress response-associated proteins, such as immunoglobulin light chain and PAP-1 or $\beta_2$-microglobulin; enzymes and enzyme inhibitors, such as PAI-I, PAI-I-urokinase, PAI-I-tPA, prourokinase, lipoprotein lipase, plasminogen, $\alpha$-amylase, $\beta$-amylase, $\alpha_1$-microglobulin, and lysozyme, and inhibitors thereof; drugs and poisons, such as aminoglycoside, polymyxin B, aprotinin, and trichosantin; carrier proteins, such as albumin, lactoferrin, hemoglobin, odorant-binding protein, transthyretin, and L-FABP; and receptor-associated proteins (RAP), such as cytochrome c, calcium ($Ca^{2+}$), advanced glycation end products (AGE), cubilin, and $Na^+$-$H^+$ exchanger isoform 3 (NHE3). The term "fragment capable of binding . . . " refers to a fragment of an aforementioned substance containing a site binding to human megalin.

An anti-human megalin antibody or the like can be bound to a solid support of a ligand capable of binding to human megalin by a method that has heretofore been well-known in the art. When an anti-human megalin antibody is bound to a well of a microtiter plate, for example, a solution comprising about 3 to 10 μg/ml antibody (and preferably about 5 μg/ml) relative to a ligand capable of binding to human megalin may be applied to a solid support, and the resultant is then allowed to stand at 4° C. overnight (and preferably 12 hours or longer). The recommended concentration range of a solid support described above was theoretically determined when immobilizing a full-length antibody to a solid support. The theoretical formula is as follows, and it is employed when immobilizing an antibody via physical adsorption:

$$Q=(2/\sqrt{3}) \cdot (MW/N) \cdot (2r)^{-2} \cdot 10^9 \text{ (ng/cm}^2\text{)}$$

Q: molecular weight density (ng/cm²)
MW: molecular weight (dalton: Da)
N: Avogadro's number=$6 \cdot 10^{23}$ (mole$^{-1}$)
r: Stokes radius of molecule=$(R \cdot T_{20})/(6 \cdot \pi \eta_{20} \cdot D_{20} \cdot N)$(cm)
R: gas constant=$8.3 \cdot 10^7$ (g·cm²·sec$^{-2}$·°K$^{-1}$·mole$^{-1}$)
$T_{20}$: room temperature (20° C.)=293° K
$\eta_{20}$: viscosity of water at 20° C.=$1 \cdot 10^{-2}$ (g·cm$^{-1}$·sec$^{-1}$)
$D_{20}$: diff. coeff. of molecular ref. to water at 20° C. (cm²·sec$^{-1}$)

When immobilizing a ligand capable of binding to human megalin, accordingly, theoretical concentrations for solid supports influenced by variable factors such as individual molecular weight are determined, and concentrations vary depending on individual solid support molecular species and solid support surface configurations. Thus, solid support concentration is not limited to the range described above. When solid support adsorption results from covalent binding, the present invention is applicable. In such a case, however, the number of functional groups existing on the adsorption surface and used for covalent binding and other conditions are taken into consideration. Thus, solid support concentration is not limited. In order to block a protein non-specific adsorption site after binding, blocking is carried out with the use of bovine serum albumin (hereafter abbreviated as "BSA"), casein, or the like in accordance with a conventional technique. When a solid support is a magnetic particle, the same procedure as that used with the case of the microtiter plate is carried out.

A ligand capable of binding to human megalin, such as an anti-human megalin antibody, bound to a solid support as described above is allowed to react with a urine specimen, and human megalin in the urine specimen is bound to a solid support through the ligand capable of binding to human megalin bound to a solid support by the ligand-receptor binding reaction, such as an antigen-antibody reaction. Specifically, a composite of the first ligand capable of binding to human megalin, such as an anti-human megalin antibody, bound to a solid support with human megalin is formed. This antigen-antibody reaction can be carried out preferably at 4° C. to 45° C., more preferably 20° C. to 40° C., and further preferably 25° C. to 38° C. The duration of the reaction is preferably about 10 minutes to 18 hours, more preferably 10 minutes to 1 hour, and further preferably 30 minutes to 1 hour.

After washing, the second ligand capable of binding to human megalin is then allowed to react with human megalin in the specimen bound to a solid support. Specifically, a composite of the first ligand capable of binding to human megalin, such as an anti-human megalin antibody, bound to a solid support, human megalin, and the second ligand capable of binding to human megalin is formed. An anti-human megalin antibody or another substance can be used as the second ligand capable of binding to human megalin, as with the case of the first ligand capable of binding to human megalin. When both the first ligand capable of binding to human megalin and the second ligand capable of binding to human megalin are anti-human megalin monoclonal antibodies, however, an epitope recognized and bound by the first anti-human megalin antibody should be different from that recognized and bound by the second anti-human megalin antibody. Combinations of the first anti-human megalin antibody and the second anti-human megalin antibody can be any of the following: a monoclonal antibody and a monoclonal antibody, a monoclonal antibody and a polyclonal antibody, a polyclonal antibody and a monoclonal antibody, and a polyclonal antibody and a polyclonal antibody. The reaction can be carried out preferably at 4° C. to 45° C., more preferably 20° C. to 40° C., and further preferably 25° C. to 38° C. The duration of the reaction is preferably about 10 minutes to 18 hours, more preferably 10 minutes to 1 hour, and further preferably 30 minutes to 1 hour. Thus, the second ligand capable of binding to human megalin can be bound to a solid support through human megalin and the first ligand capable of binding to human megalin.

After washing, the second ligand capable of binding to human megalin, such as the second anti-human megalin antibody, bound to a solid support is then measured by various techniques that are commonly used in the field of immunoanalysis. For example, the second ligand capable of binding to human megalin is labeled with an enzyme, fluorescence, biotin, or radioactive label to prepare an enzyme-labeled substance, and the label is measured. Thus, the second ligand capable of binding to human megalin bound to a solid support can be measured. Labeling with an enzyme or fluorescence is particularly preferable. Examples of enzymes include, but are not limited to, peroxidase, alkaline phosphatase, β-galactosidase, and glucose oxidase. An example of fluorescence is fluorescein isothiocyanate (FITC), although fluorescence is not limited thereto. Labeling can be detected by allowing a corresponding substrate to react with an enzyme-labeled substance and measuring a pigment, fluorescence, luminescence, or the like resulting from the reaction. When the second ligand capable of binding to human megalin is not labeled, alternatively, the labeled third antibody reacting with the second ligand capable of binding to human megalin is allowed to react, and the third antibody is measured based on such labeling. Thus, the second ligand capable of binding to human megalin can be measured.

An anti-human megalin antibody used for immobilization or labeling may be an immunoglobulin fragment specific to human megalin, such as Fab or F(ab')$_2$, or a recombinant antibody, such as scFv, dsFv, diabody, or minibody which has been expressed as a recombinant substance. The term "antibody" used in the present invention also refers to such a fragment specific to human megalin. A method for preparing such a fragment is well-known in the art.

The above method comprises two steps of: allowing the first ligand capable of binding to human megalin, such as an anti-human megalin antibody, bound to a solid support to react with a specimen, followed by washing, and then allowing the second ligand capable of binding to human megalin to react therewith. Alternatively, a step of allowing the first ligand capable of binding to human megalin, such as an anti-human megalin antibody, bound to a solid support to react with a specimen and a step of allowing the second ligand capable of binding to a specimen and human megalin to react may be carried out simultaneously as a single step.

The present invention also includes a method for measuring human megalin in a specimen using human megalin bound to a solid support or a partial fragment thereof and a ligand capable of binding to human megalin, wherein a specimen is allowed to react with a ligand capable of binding to human megalin, the reaction product is allowed to react with the human megalin bound to a solid support, the ligand capable of binding to human megalin bound to a solid support is measured, and human megalin in a specimen is competitively quantified based on a decrease in the ligand capable of binding to human megalin bound to a solid support. In order to implement this method, it is necessary to bind human megalin to a solid support, and this can be carried out by the method for binding a substance to a solid support as described above. A partial fragment of human megalin is not limited, and a partial fragment of human megalin to which a ligand capable of binding to human megalin can bind may be used. A partial fragment of human megalin can be prepared from a partial sequence of the amino acid sequence of human megalin as shown in SEQ ID NO: 2 via chemical synthesis or genetic engineering. Ligands capable of binding to human megalin described above can be used, with an anti-human megalin antibody being particularly preferable. In the competitive technique, the amount of human megalin bound to a solid support to be used or a partial fragment of human megalin and a ligand capable of binding to human megalin is important. Since the competitive technique is known, a procedure can be adequately determined based on a conventional technique.

Further, the present invention includes a method for measuring human megalin in a specimen using a ligand capable of binding to human megalin comprising allowing a specimen to react with a ligand capable of binding to human megalin bound to a particle to cause an agglutination reaction, and measuring human megalin based on the degree of the resulting agglutination.

Examples of particles used in such method include latex particles each having a diameter of 0.05 to 10 μm and preferably 0.1 to 0.4 μm and gelatin particles and animal blood erythrocytes each having a diameter of 0.5 to 10 μm. Methods of binding an antibody to a particle are well-known in the art, and physical adsorption or covalent binding may be used.

In the above described method, particles to which anti-human megalin antibodies have been bound are mixed with the specimen on, for example, a black glass slide, and particles precipitated upon agglutination are observed. Thus, human megalin in the specimen can be detected. By measuring the absorbance of such agglutination, human megalin can be quantified. Further, detection can be carried out via pulse immunoassay.

According to the method for measuring human megalin of the present invention, human megalin fragments can be measured, in addition to intact human megalin.

A renal disorder can be detected by using human megalin in urine sampled from a subject who is a patient with a renal disorder as a marker. Examples of renal disorders include diabetic nephropathy, and in particular, type II diabetic nephropathy, IgA nephropathy, nephrotic syndrome, chronic glomerulonephritis, membranous nephropathy, ANCA-associated glomerulonephritis, systemic erythematodes (lupus glomerulonephritis), Henoch-Schönlein purpura nephritis, interstitial glomerulonephritis, crescentic glomerulonephritis, focal glomerulosclerosis, nephrosclerosis, acute renal failure, chronic renal failure, renal amyloidosis, scleroderma renal crisis, interstitial glomerulonephritis caused by Sjogren's syndrome, and drug nephropathy. An increased amount of megalin excreted into the urine is observed at an early stage of nephropathy, and thus a renal disorder can be detected at an earlier stage than is possible with the use of existing diagnostic markers for renal disorders. Since the amount of human megalin excreted into the urine is increased due to proximal renal tubular disorders and failure of resorption capacity in the lesion, measurement of human megalin in urine can be utilized to determine a site of renal disorder. In addition, measurement of human megalin in urine can be utilized for evaluation of the activity of progressive renal disorders (e.g., the degree of progression or prognosis). Further, measurement of human megalin in urine can be utilized for prognostic prediction of a renal disorder and judgment of the degree of disorder (i.e., the progression of pathological conditions), which enables prevention of a renal disorder at an earlier stage. In the present invention, the term "detection of a renal disorder" also refers to inspection of a renal disorder, and such detection enables prognostic prediction of a renal disorder such as diabetic nephropathy, and in particular, type II diabetic nephropathy or IgA nephropathy. Also, the degree of a renal disorder such as diabetic nephropathy, and in particular, type II diabetic nephropathy or IgA nephropathy, can be evaluated. Human megalin is excreted into the urine at an early stage of a renal disorder, the amount thereof excreted increases as the severity of the renal disorder increases, and the concentration of human megalin in urine increases. When the human megalin concentration in urine is high in a subject who is a patient with a renal disorder, it can be predicted that the subject has a poor prognosis. Also, tubular dysfunction can be detected with the use of human megalin in urine as a marker to evaluate the degree of tubular dysfunction. Specifically, the prognostic prediction of a renal disorder described above is conducted so as to evaluate tubular dysfunction, and the evaluation of the degree of renal disorder is conducted so as to evaluate the degree of tubular dysfunction.

EXAMPLES

The present invention is described in detail with reference to the following examples, although the present invention is not limited to these examples.

Example 1

Preparation of Anti-Human Megalin Mouse Monoclonal Antibody

A mouse was intraperitoneally immunized with 50 μg of human megalin and an adjuvant several times, and the elevated serum titer thereof was confirmed. The spleen was extracted 3 days after booster immunization (in the vein) to obtain splenic cells. The obtained suplenic cells were fused to mouse myeloma cells (10:1) in the presence of polyethylene glycol 3500 to prepare hybridoma cells. The resulting cells were cultured in $CO_2$ at 37° C. for 1 week, and the presence of anti-human megalin antibodies in the culture supernatant was inspected. The cells in positive wells in which antibody production was observed were diluted via limiting dilution, the resultant was cultured for 2 weeks, and the presence of anti-human megalin antibodies in the culture supernatant was inspected in the same manner. Further, cells in positive wells in which antibody production was observed were subjected to limiting dilution again and culture was conducted in the same manner. Cells in which anti-human megalin antibodies had already been produced at this phase were cultured in a flask, some of the resultant was suspended in fetal calf serum (FCS) containing 10% dimethyl sulfoxide (DMSO) ($5 \times 10^6$ cells/ml), and the resultant was stored in liquid nitrogen.

Subsequently, supernatants in the wells were used to inspect the reactivity of antibodies produced in the culture supernatant to human megalin. Human megalin was dissolved in 140 mM NaCl, 2.7 mM KCl, 10 mM $Na_2HPO_4$, 1.8 mM $KH_2PO_4$ (pH 7.3) (hereafter abbreviated as "PBS (pH 7.3)"). The human megalin/PBS (pH 7.3) solution was applied to wells of a plastic microtiter plate (Nunc-Immuno™ Module F8 Maxisorp™ Surface plate, manufactured by Nalge Nunc International) at 100 μl/well, and human megalin was immobilized on the microtiter plate at 3 pmol/well at 4° C. for 12 hours. The human megalin/PBS (pH 7.3) solution that had been applied to the wells was removed via decantation 12 hours later, a wash solution was applied to the wells of the microtiter plate at 200 μl/well, the wash solution was removed via decantation, and human megalin excessively adsorbed in the wells was washed. This process of washing was carried out twice in total. Thereafter, a blocking solution was applied to the antigen-immobilized plate at 200 μl/well to block the wells of the human-megalin-immobilized microtiter plate at 4° C. for 12 hours. After twelve hours lapsed, the plate was stored at 4° C. In order to confirm reactivity of antibodies in the culture supernatant, the human-megalin-immobilized microtiter plate resulting after blocking was used. The hybridoma culture supernatant was applied to wells of the human-megalin-immobilized microtiter plate at 100 μl/well, and the plate was heated at 37° C. for 1 hour. Thereafter, the culture supernatant that had been applied to the wells was removed via decantation, a wash solution was applied to the wells of the microtiter plate at 200 μl/well, the wash solution was removed via decantation, and insides of the wells were washed. This process of washing was carried out three times in total. Thereafter, peroxidase-conjugated goat anti-mouse immunoglobulin (manufactured by DAKO) was applied to the wells at 100 μl/well (2,000-fold diluted, 0.55 μg/ml), and the plate was heated at 37° C. for 1 hour. The enzyme-labeled antibodies were diluted with a diluent for enzyme labeled antibodies. Thereafter, the enzyme-labeled antibodies that had been applied to the wells were removed via decantation, a wash solution was applied to the wells of the microtiter plate at 200 μl/well, the wash solution was removed via decantation, and insides of the wells were washed. This process of washing was carried out three times in total. Thereafter, a solution of 3,3',5,5'-tetramethylbenzidine (hereafter abbreviated as "TMB") (TMB One-Step Substrate System, manufactured by DAKO) was applied to the wells at 100 μl/well as a substrate solution for the peroxidase enzyme reaction, and the resultant was allowed to stand at 25° C. for 30 minutes. Immediately thereafter, a reaction stop solution was added to the substrate solution in the wells at 100 μl/well to terminate the enzyme reaction in the wells. Thereafter, the absorbance of the wells was measured, the absorbance at 630 nm was subtracted from that at 450 nm, and the resulting value was designated as an indicator for reactivity evaluation.

As a result, monoclonalized hybridoma cells in which the anti-human megalin antibody exhibited potent reactivity to the immobilized human megalin were selected, and the immunoglobulin class and subclass in the culture supernatant were inspected for each clone from 100 μl of the culture supernatant stock solution using the mouse immunoglobulin typing kit (Wako Pure Chemical Industries, Inc.). Based on the results, cells of the IgG class were selected from the resulting monoclonal cell library and transferred for the process of ascites production described below.

Subsequently, these cells were cultured in a 25-ml flask and further cultured in a 75-ml flask. The resulting cells were injected intraperitoneally into a pristane-treated mouse to sample the ascites.

Example 2

Preparation of Anti-Human Megalin Mouse Monoclonal (IgG) Antibody

The obtained ascites (10 ml) was mixed with an opacified blood serum-treating agent (FRIGEN (registered trademark) II: manufactured by Kyowa Pure Chemical Co., Ltd.) at a ratio of 1.5:1 by volume, and the resultant was shaken and stirred for 1 to 2 minutes to delipidize the ascites. The ascites was centrifuged using a centrifuge at 3,000 rpm (1,930×g) for 10 minutes, and the centrifuged supernatant of clarified ascites (10 ml) was fractionated. The centrifuged supernatant of ascites (10 ml) was subjected to ammonium sulfate fractionation (final concentration: 50% saturated ammonium sulfate) in an ice bath for 1 hour, and the precipitated immunoglobulin fraction was suspended and dissolved in PBS. This process of ammonium sulfate fractionation was carried out twice in total to obtain a crude immunoglobulin fraction from ascites. The resulting crude immunoglobulin fraction (10 ml) was mixed with an equivalent amount of 20 mM sodium phosphate (pH 7.0; hereafter referred to as "20 mM NaPB (pH7.0)") and then subjected to affinity purification using a protein G column (HiTrap Protein G HP, 5 ml; manufactured by GE Healthcare). The sample was adsorbed on a protein G column, 50 ml of 20 mM NaPB (pH 7.0) was flushed through the protein G column, and contaminants other than IgG in the sample were removed by washing. Thereafter, affinity-adsorbed IgG on the protein G column was eluted with 0.1 M glycine-HCl (pH 2.7), and the elution fraction immediately after elution from the column was neutralized with 1M Tris (hydroxymethyl)aminomethane-HCl (pH 9.0) (hereafter, "Tris(hydroxymethyl)aminomethane" is abbreviated as "Tris") and then recovered. After neutralization, the affinity-purified product was dialyzed against PBS in an amount 500 times greater than that of the purified product by volume at 4° C. for 6 hours, and this process of dialysis was carried out twice in total. The dialysis membrane used for dialysis was a cellulose tube for dialysis (manufactured by Viskase Companies). The resulting IgG elution fraction was designated as a purified anti-human megalin monoclonal antibody and subjected to storage at 4° C. and procedures described below. The process of purification was performed by connecting the aforementioned protein G column to the BioLogic LP System (manufactured by Bio Rad Laboratories) at a constant flow rate of 1 ml/min.

Example 3

Measurement of Human Megalin in Urine

Figure 2:
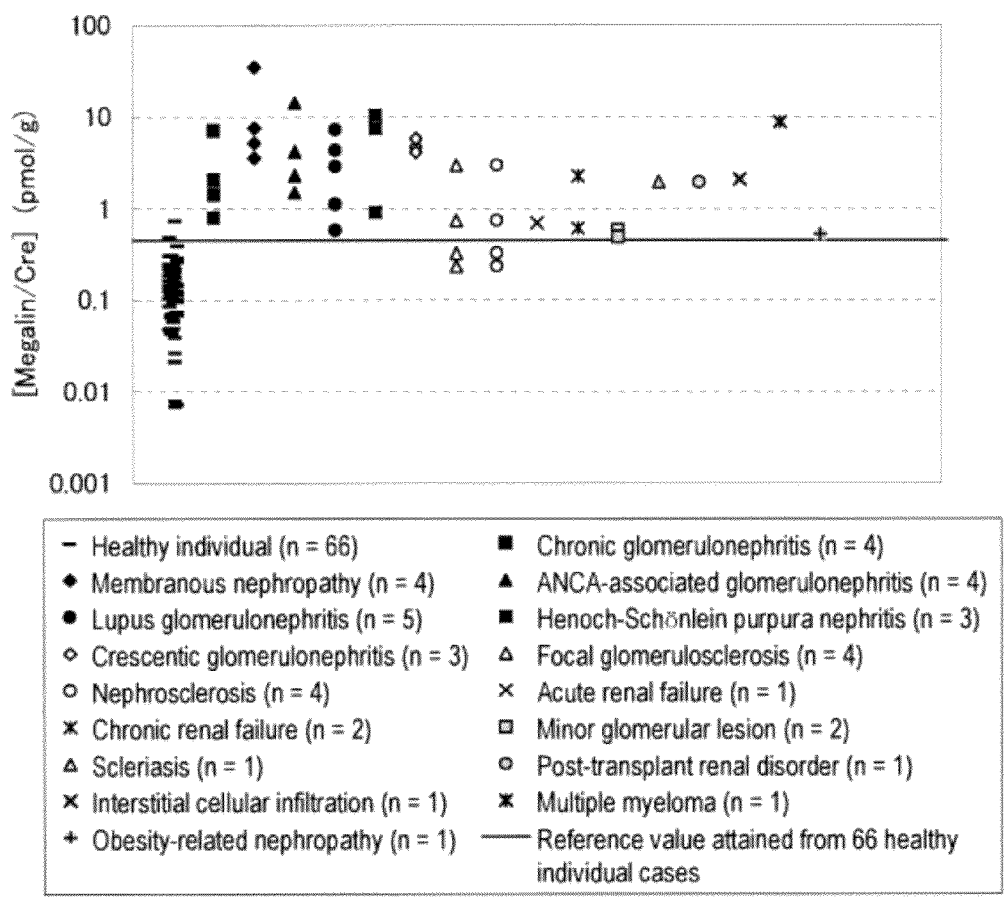
FIG. 2 shows the results of measurement of the amount of human megalin excreted into the urine (creatinine correction value) in several other nephropathy cases.

Two types of anti-human megalin monoclonal antibodies recognizing different epitopes were used to measure the amount of human megalin excreted into the urine. A microtiter plate on which anti-human megalin monoclonal antibodies had been immobilized and anti-human megalin monoclonal antibodies labeled with alkaline phosphatase (hereafter abbreviated as "ALP") were used to measure the human megalin concentration in urine. At the outset, 90 µl of primitive urine was mixed with 10 µl of a solution comprising 2 M Tris-HCl, 0.2 M ethylenediamine-N,N,N',N'-tetraacetic acid (hereafter abbreviated as "EDTA"), and 10% (vol/vol) polyethylene glycol mono-p-isooctylphenyl ether (hereafter abbreviated as "Triton X-100") (pH 8.0), and 100 µl of the resulting mixture was applied to wells of the microtiter plate on which the anti-human megalin monoclonal antibodies had been immobilized (FluoroNunc™ Module F16 Black-Maxisorp™ Surface plate, manufactured by Nalge Nunc International). The resultant was allowed to stand at 37° C. for 1 hour, the urine sample solution that had been applied to the wells was removed via decantation, 137 mM NaCl, 2.68 mM KCl, 25 mM Tris-HCl, and 0.05% (v./v.) Tween 20 (hereafter abbreviated as "TBS-T") were applied to wells of the microtiter plate at 200 µl/well, and TBS-T was removed via decantation, followed by washing. The process of washing was carried out three times in total. Thereafter, the solution of ALP-labeled anti-human megalin monoclonal antibodies (0.5 ng/ml) was applied at 100 µl/well. The ALP-labeled anti-human megalin monoclonal antibodies were prepared in TBS-T containing 0.2% (wt./v.) casein (hereafter referred to as a diluent for labeled antibodies). The resultant was allowed to stand at 37° C. for 1 hour, the solution of ALP-labeled antibodies that had been applied to the wells was removed via decantation, TBS-T was applied to wells of the microtiter plate at 200 µl/well, and TBS-T was removed via decantation, followed by washing. The process of washing was carried out four times in total. Subsequently, 20 mM Tris-HCl and 1 mM $MgCl_2$ (pH 9.8) (hereafter referred to as an "assay buffer") were applied to wells of the microtiter plate at 200 µl/well, and the assay buffer was removed via decantation, followed by washing. The process of washing was carried out twice in total. Subsequently, CDP-Star (registered trademark) chemiluminescent substrate for alkaline phosphatase ready-to-use (0.4 mM) with Emerald-II™ enhancer (ELISA-Light™ System, manufactured by Applied Biosystems) was applied to the wells as a substrate solution for ALP enzyme reaction at 100 µl/well, and the resultant was allowed to stand at 37° C. for 30 minutes while shielded from light. Immediately thereafter, the accumulated emission intensity of the wells for 1 second was measured, and the resulting value was designated as an indicator for measurement and evaluation of full-length human megalin in urine. The chemiluminescence intensity was measured using the Microplate Luminometer Centro LB960 and MicroWin2000 software (manufactured by Berthold). As the reference sample for the calibration curve, native human megalin extracted from the kidney was used. The results of actual clinical measurement of human megalin in urine are shown in FIG. 1 and FIG. 2. Backgrounds of patients subjected to measurement, patients with type II diabetic nephropathy (71 cases), patients with IgA nephropathy (81 cases), and patients with nephrotic syndrome (18 cases), are shown in Table 1.

TABLE 1

| Parameters | 1: Healthy individual | 2: Type II diabetic nephropathy | 3: IgA nephropathy | 4: Nephrotic syndrome |
| --- | --- | --- | --- | --- |
| Number (n) | 66 | 71 | 81 | 18 |
| Sexuality (F/M) | 20/46 | 26/45 | 57/24 | 6/12 |
| Age | 31.5 ± 10.3 | 65.5 ± 11.8 | 32.2 ± 10.5 | 52.9 ± 15.3 |
| BMI (kg/m$^2$) | 20.5 ± 1.8 | 25.0 ± 5.5 | 21.0 ± 2.9 | 24.5 ± 2.9 |
| Systolic blood pressure (mmHg) | 108.5 ± 9.8 | 129.3 ± 14.7 | 112.3 ± 13.9 | 117.7 ± 13.1 |
| Diastolic blood pressure (mmHg) | 64.5 ± 7.4 | 77.1 ± 9.8 | 64.9 ± 10.4 | 69.4 ± 8.6 |
| Albumin excreted into the urine (mg/g creatinine in urine) | 4.5 ± 2.5 | 2398.2 ± 8459.5 | 1204.5 ± 3136.5 | 12683.8 ± 17513.4 |
| HbA1c (%) | — | 6.8 ± 1.6 | — | — |
| Fasting blood sugar level (mg/dl) | 75.2 ± 7.7 | 148.4 ± 55.7 | — | — |
| eGFR (ml/min/1.73 m$^2$) | 90.2 ± 15.2 | 67.5 ± 18.7 | 84.0 ± 22.6 | 71.1 ± 23.1 |

FIG. 1 and Table 2 show the results of actual clinical measurement regarding type II diabetic nephropathy, IgA nephropathy, and nephrotic syndromes.

TABLE 2

|  | Healthy individual | Type II diabetic nephropathy | IgA nephropathy | Nephrotic syndrome |
|---|---|---|---|---|
| Reference value Over (number of cases) | 2/66 cases | 43/71 cases | 56/81 cases | 17/18 cases |
| Reference value Over (%) | 3.0% | 60.6% | 69.1% | 94.4% |

As shown in FIG. 1 and Table 2, the amount of megalin excreted into the urine was found to have significantly increased in disease groups, compared with healthy individuals. The amount of megalin excreted into the urine was evaluated by dividing the megalin concentration in urine by the creatinine concentration in urine to correct the concentration and evaluating the obtained creatinine correction value. This is commonly used for a biomarker in urine in order to confirm that the results have not been influenced by the concentration ratio at the time of urine excretion. As a reference value for the amount of megalin excreted into the urine determined by 66 healthy individuals (normal range), 448 fmol (megalin in urine)/g (creatinine in urine) was employed. That is, a 95% confidence interval was calculated based on the normal distribution of megalin concentrations in urine of 66 healthy individuals (i.e., the creatinine correction value), the upper limit of the 95% confidence interval was 448 fmol (megalin in urine)/g (creatinine in urine), and the determined value was used as a reference value for the megalin concentrations in urine. It should be noted that the reference value obtained may vary depending on modification of methods for setting standards for measurement platform or reference material, and the obtained value would not be permanently used as an absolute cut-off value. Specifically, the cut-off value is not particularly limited to 448 fmol (megalin in urine)/g (creatinine in urine). However, the results attained in this example can be conceived as representing a reference value with consistent validity. As shown in FIG. 2, the amount of megalin excreted into the urine is higher in patients with chronic glomerulonephritis, membranous nephropathy, ANCA-associated glomerulonephritis, lupus glomerulonephritis, Henoch-Schönlein purpura nephritis, crescentic glomerulonephritis, focal glomerulosclerosis, nephrosclerosis, acute renal failure, chronic renal failure, minor glomerular lesion, scleriasis, post-transplant renal disorder, interstitial cellular infiltration, multiple myeloma, and obesity-related nephropathy, compared with healthy individuals, although the number of such cases is small. A majority of cases exhibit high megalin levels in urine exceeding the reference value for megalin level in urine described above. Thus, the megalin level in urine was found to be useful as a diagnostic marker for renal disorders in various diseases mentioned above.

Example 3 demonstrates that human megalin in urine can be specifically measured and evaluated and the amount of human megalin excreted into the urine increased with type II diabetic nephropathy, IgA nephropathy, nephrotic syndrome, and other nephropathy cases. It was thus considered that human megalin in urine is effective for recognition of pathological conditions and diagnosis of nephropathy.

Example 4

Comparison of usefulness of megalin level in urine and other markers for renal disorder for prognostic prediction and diagnosis, when prognosis determined by histological classification of IgA nephropathy (59 cases) via renal biopsy is used as indicator (significant difference test)

Regarding the data on the concentration of human megalin excreted into the urine from the 81 IgA nephropathy cases obtained in Example 3, 59 samples subjected to renal biopsy were further subjected to sub-analysis using the prognosis determined by histological classification attained by renal biopsy as an indicator. This analysis was intended to examine whether or not the amount of megalin excreted into the urine could serve as an indicator for prognostic prediction, as prognosis becomes poorer based on the histological prognostic classification of IgA nephropathy. Backgrounds of patients with IgA nephropathy (59 cases) are shown in Table 3 in accordance with the prognosis determined by histological classification attained by renal biopsy.

TABLE 3

| Parameters | 1: Healthy individual | 2: IgA nephropathy (Good prognosis and relatively good prognosis groups) | 3: IgA nephropathy (Relatively poor prognosis group) | 4: IgA nephropathy (Poor prognosis group) |
|---|---|---|---|---|
| Number (n) | 66 | 8 | 29 | 22 |
| Sexuality (F/M) | 20/46 | 6/2 | 25/4 | 17/5 |
| Age | 31.5 ± 10.3 | 28.3 ± 8.1 | 29.8 ± 6.1 | 34.2 ± 8.6 |
| BMI (kg/m$^2$) | 20.5 ± 1.8 | 20.5 ± 2.6 | 19.5 ± 2.8 | 21.6 ± 2.8 |
| Systolic blood pressure (mmHg) | 108.5 ± 9.8 | 104.0 ± 16.1 | 107.3 ± 8.2 | 118.0 ± 16.6 |
| Diastolic blood pressure (mmHg) | 64.5 ± 7.4 | 57.6 ± 3.6 | 63.1 ± 10.5 | 64.6 ± 12.8 |
| Albumin excreted into the urine (mg/g creatinine in urine) | 4.5 ± 2.5 | 1474.0 ± 2929.6 | 1113.8 ± 3026.9 | 493.4 ± 413.5 |
| HbA1c (%) | — | — | — | — |
| Fasting blood sugar level (mg/dl) | 75.2 ± 7.7 | — | — | — |
| eGFR (ml/min/1.73 m$^2$) | 90.2 ± 15.2 | 105.6 ± 18.0 | 88.6 ± 20.5 | 67.6 ± 19.6 |

Figure 3:
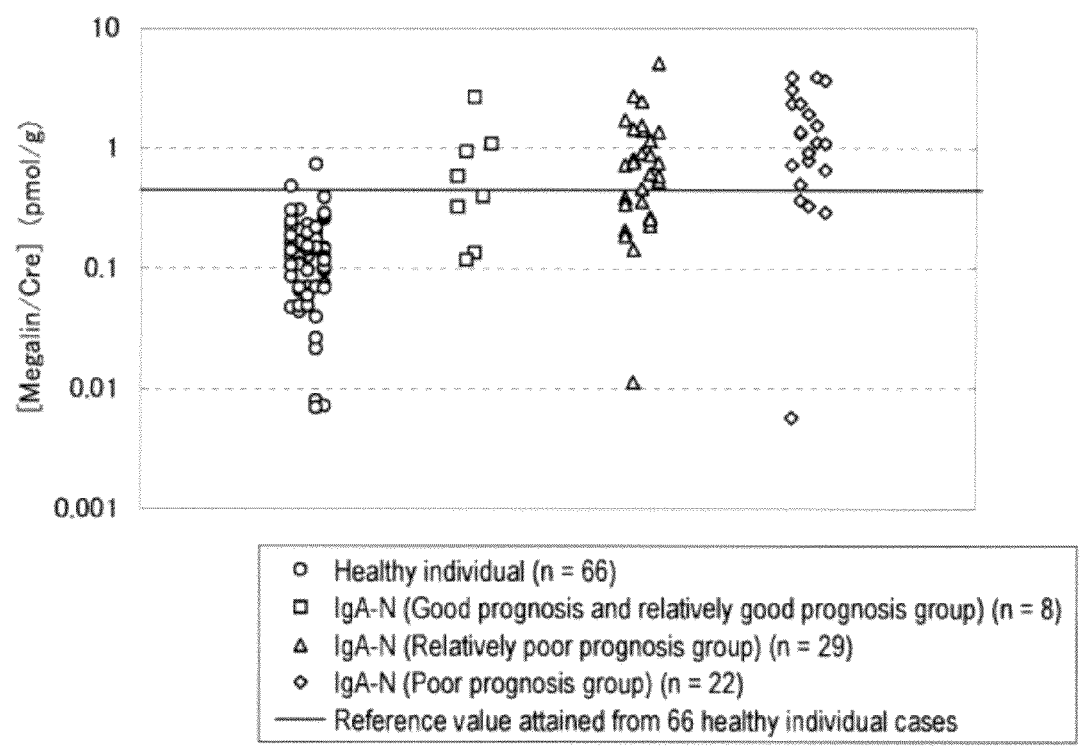
FIG. 3 shows the results of measurement of the amount of human megalin excreted into the urine (creatinine correction value) in cases of IgA nephropathy (59 cases) based on histological prognosis classification (prognosis achieved by histological classification of renal biopsies).

FIG. 3 and Table 4 show the results of sub-analysis of the amount of megalin excreted into the urine based on the prognosis determined by histological classification of IgA nephropathy attained by renal biopsy.

TABLE 4

| | IgA nephropathy | | | |
|---|---|---|---|---|
| | Healthy individual | Good prognosis and relatively good prognosis | Relatively poor diagnosis | Poor prognosis |
| Reference value Over (number of cases) | 2/66 cases | 4/8 cases | 19/29 cases | 17/22 cases |
| Reference value Over (%) | 3.0% | 50.0% | 65.5% | 77.3% |

As shown in FIG. 3 and Table 4, the amount of megalin excreted into the urine was found to increase and the percentage of cases with abnormally high megalin levels in urine was found to increase as the prognosis became poorer. Other diagnostic markers for renal diseases and megalin level in urine were subjected to similar analysis, and the results were compared. The results are shown in Table 5.

TABLE 5

| | | IgA nephropathy | | | |
|---|---|---|---|---|---|
| | | Good prognosis and relatively good prognosis | Relatively poor diagnosis | Poor prognosis | Total |
| Megalin in urine | Reference value Over (number of cases) | 4/8 cases | 19/29 cases | 17/22 cases | 40/59 cases |
| | Reference value Over (%) | 50.0% | 65.5% | 77.3% | 67.8% |
| Protein in urine | Reference value Over (number of cases) | 1/8 cases | 12/29 cases | 15/22 cases | 28/59 cases |
| | Reference value Over (%) | 12.5% | 41.4% | 68.2% | 47.5% |
| β2-MG in urine | Reference value Over (number of cases) | 0/8 cases | 1/29 cases | 3/22 cases | 4/59 cases |
| | Reference value Over (%) | 0.0% | 3.4% | 13.6% | 6.8% |
| α1-MG in urine | Reference value Over (number of cases) | 0/8 cases | 0/29 cases | 2/22 cases | 2/59 cases |
| | Reference value Over (%) | 0.0% | 0.0% | 9.1% | 3.4% |
| NAG in urine | Reference value Over (number of cases) | 2/8 cases | 11/29 cases | 14/22 cases | 27/59 cases |
| | Reference value Over (%) | 25.0% | 37.9% | 63.6% | 45.8% |

As shown in Table 5, megalin levels in urine for the 40 cases exceeded the reference values for 59 IgA nephropathy cases. The results indicate that megalin level in urine is the most useful marker for renal disorder screening diagnosis (Table 5).

In addition, usefulness of megalin level in urine was compared with that of other diagnostic urine markers for renal diseases in terms of prognostic prediction and diagnosis. Specifically, the outcome of IgA nephropathy was classified based on the prognosis determined by histological classification attained by renal biopsy as follows: the good prognosis and relatively good prognosis groups (score 1); the relatively poor prognosis group (score 2); and the poor prognosis group (score 3). In this case, outcomes were indicated by occurence ration of outcome which exhibited values equal to or higher than reference values (i.e., cut-off values) for each marker. Significant difference was determined by the Mann-Whitney U test and evaluated. As control diagnostic urine markers for renal disorders, β2-microglobulin in urine (cut-off: 300 μg/g creatinine in urine), α1-microglobulin in urine (cut-off: 12 mg/g creatinine in urine), N-acetyl-β-D-glucosaminidase in urine (cut-off: 6 IU/g creatinine in urine), and protein in urine (cut-off: 0.5 g/g creatinine in urine) were used, and reference values commonly used in routine medical care were employed as cut-off values for control markers. The results are shown in Table 6.

TABLE 6

| | vs. urinary protein (dominance/recessiveness) | vs. urinary protein (significant difference) | Accurate P-value |
|---|---|---|---|
| Megalin in urine | Dominant | $P < 0.001$ | 0.0003 |
| β2-MG in urine | Inferior | $P < 0.05$ | 0.0383 |
| α1-MG in urine | Inferior | $P < 0.05$ | 0.0102 |
| NAG in urine | Inferior | NS | 0.1241 |

As shown in Table 6, the megalin level in urine alone was found to be a more useful marker in prognostic prediction and diagnosis, compared with the urinary protein that is the most common diagnostic urine marker for IgA nephropathy. Complication of renal tubular disorders is considered to be a factor as a tendency in clinical findings of poor diagnosis of IgA nephropathy. At present, β2-microglobulin in urine, a1-microglobulin, and N-acetyl-β-D-glucosaminidase in urine are used as indicators for diagnosis of such complications. As shown in Table 5 and Table 6, however, the megalin level in urine was found to be the most effective marker as an indicator for diagnosis of such renal tubular complications.

Example 4 demonstrates that human megalin in urine can be specifically measured and evaluated, and the amount of human megalin excreted into the urine increases in accordance with the degree of or prognostic prediction for IgA nephropathy. The results demonstrate that human megalin in urine is effective for recognition of pathological conditions and diagnosis of IgA nephropathy.

Example 5

Comparison of Compatibility of Human Megalin in Urine and Other Markers for Renal Disorder with Putative Glomerular Filtration Rate at Stages-I to III of Diabetic Nephropathy (68 Cases) (Significant Difference Test)

The data regarding the concentration of human megalin excreted into the urine of 71 type II diabetic nephropathy cases obtained in Example 3 were subjected to sub-analysis using classification of diabetic staging as an indicator. This analysis is intended to examine whether or not the amount of megalin excreted into the urine could serve as an indicator for recognition of the degree of disorder as pathological conditions worsen, when analysis is carried out based on the staging of diabetic nephropathy. Backgrounds of patients with type II diabetic nephropathy (71 cases) in accordance with the staging of diabetic nephropathy are shown in Table 7.

exceeding the normal range (reference value) were found to account for 48.7% of the all cases at the stage of normal albuminuria before development of microalbuminuria. This indicates that the amount of megalin excreted into the urine sensitively reflects the development and progression of nephropathy and increases at an earlier stage than the current indicator for diagnosis of diabetic nephropathy (i.e., the amount of albumin excreted into the urine). It was thus demonstrated that use of megalin level in urine as a diagnostic marker for diabetic nephropathy enables prognostic prediction of type II diabetic nephropathy and accurate and early judgment of the degree of disorder (i.e., the progression of pathological conditions), and such use would be useful from the viewpoint of preventive care at an earlier stage. As the reference values for the amount of albumin excreted into the urine, microalbuminuria (cut-off: 30 to 300 mg/g creatinine in urine) and overt albuminuria (cut-off: 300 mg/g or more creatinine in urine) are used, and such values are commonly used for routine medical care.

TABLE 7

| Parameters | 1: Healthy individual | 2: Type II diabetic nephropathy (stage-I: preceding stage of nephropathy) | 3: Type II diabetic nephropathy (stage-II: early stage of nephropathy) | 4: Type II diabetic nephropathy (stage-III: overt nephropathy) |
|---|---|---|---|---|
| Number (n) | 66 | 39 | 17 | 15 |
| Sexuality (F/M) | 20/46 | 16/23 | 5/12 | 5/10 |
| Age | 31.5 ± 10.3 | 65.1 ± 12.0 | 63.8 ± 11.7 | 68.7 ± 11.6 |
| BMI (kg/m$^2$) | 20.5 ± 1.8 | 24.4 ± 5.1 | 25.4 ± 6.4 | 26.1 ± 5.7 |
| Systolic blood pressure (mmHg) | 108.5 ± 9.8 | 124.9 ± 10.8 | 134.4 ± 17.4 | 135.5 ± 17.4 |
| Diastolic blood pressure (mmHg) | 64.5 ± 7.4 | 77.8 ± 8.8 | 75.6 ± 12.6 | 76.9 ± 9.4 |
| Albumin excreted into the urine (mg/g creatinine in urine) | 4.5 ± 2.5 | 10.2 ± 6.3 | 87.4 ± 56.4 | 11226.0 ± 15872.8 |
| HbA1c (%) | — | 7.0 ± 1.6 | 6.6 ± 0.9 | 67. ± 2.2 |
| Fasting blood sugar level (mg/dl) | 75.2 ± 7.7 | 74.0 ± 13.8 | 70.1 ± 14.9 | 44.8 ± 19.4 |
| eGFR (ml/min/1.73 m$^2$) | 90.2 ± 15.2 | 74.0 | 70.1 | 44.8 |

Figure 4:
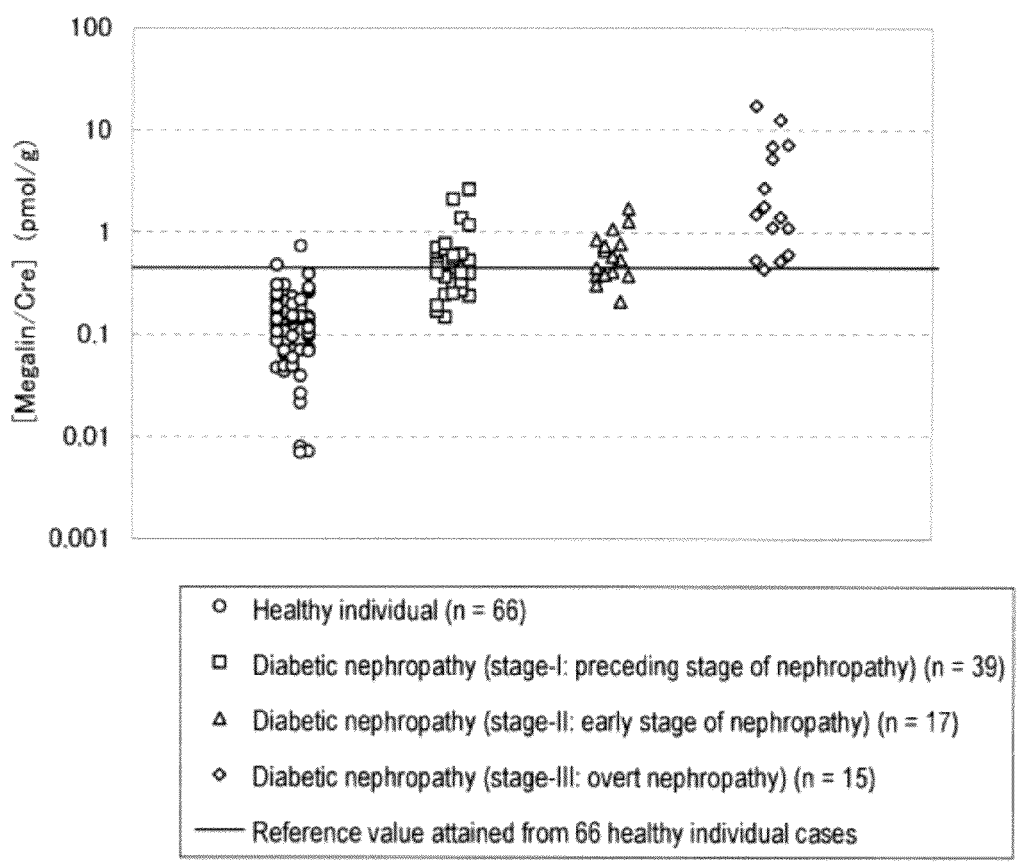
FIG. 4 shows the results of measurement of the amount of human megalin excreted into the urine (creatinine correction value) in cases of type II diabetic nephropathy (71 cases) classified in accordance with albuminuria classification (classification based on severity of disorder) in accordance with staging of diabetic nephropathy.

The results of sub-analysis of the amount of megalin excreted into the urine based on the staging of diabetic nephropathy are shown in FIG. 4 and Table 8.

TABLE 8

| | | Type II diabetic nephropathy | | |
|---|---|---|---|---|
| | Healthy individual | Stage-I (preceding stage of nephropathy) | Stage-II (early stage of nephropathy) | Stage-III (overt nephropathy) |
| Reference value Over (number of cases) | 2/66 cases | 19/39 cases | 10/17 cases | 14/15 cases |
| Reference value Over (%) | 3.0% | 48.7% | 58.8% | 93.3% |

As shown in FIG. 4 and Table 8, the amount of megalin excreted into the urine was found to increase and the percentage of cases exhibiting abnormally high megalin levels in urine was found to be elevated, as the pathological conditions worsened.

Figure 5:
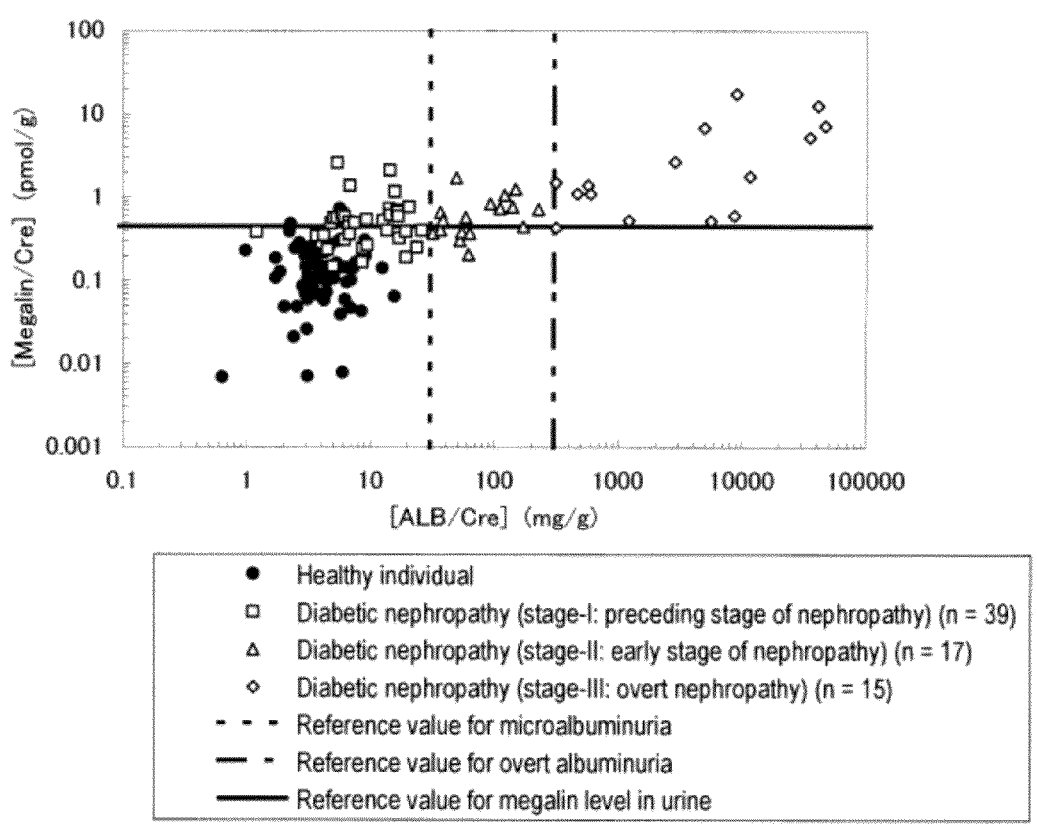
FIG. 5 shows the correlation between the albumin concentration in urine (creatinine correction value) and the human megalin concentration in urine (creatinine correction value) in cases of healthy individuals (66 cases) and in cases of type II diabetic nephropathy (71 cases) in accordance with staging of diabetic nephropathy.
Figure 6:
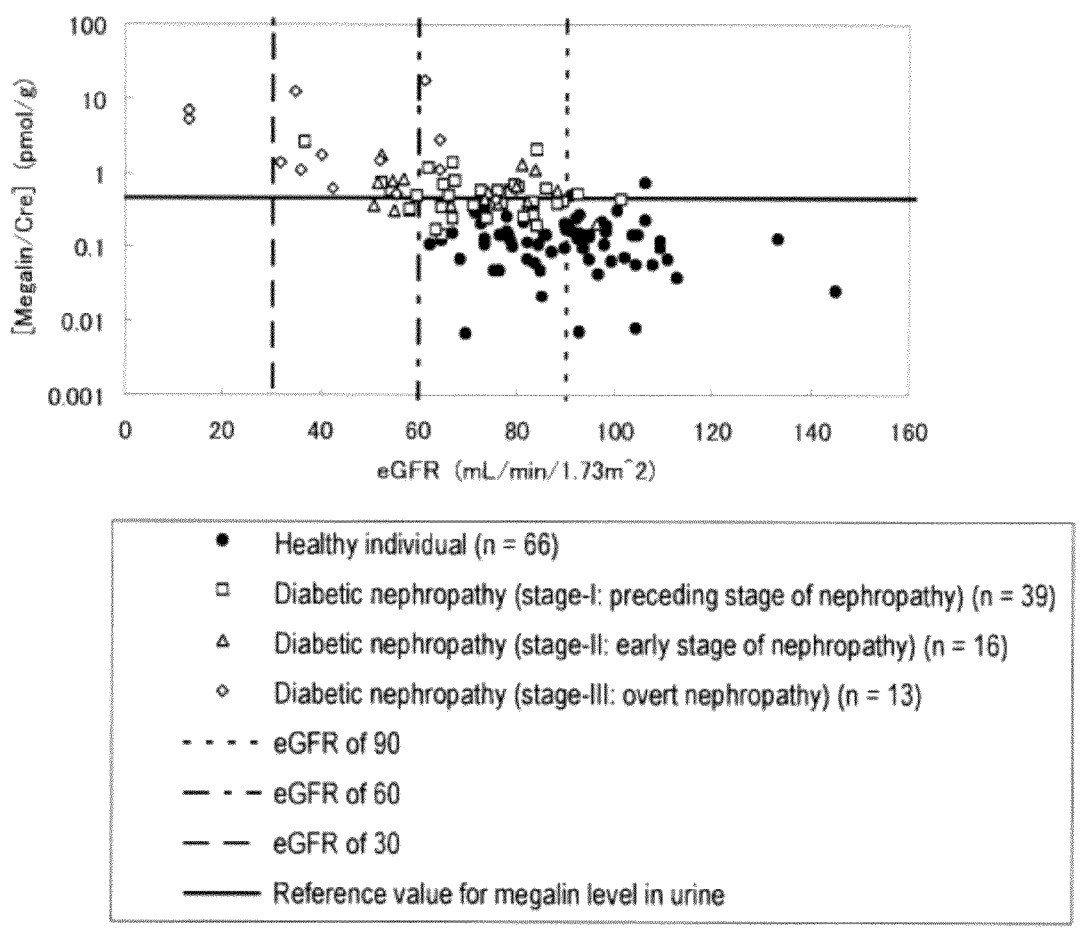
FIG. 6 shows the compatibility of the human megalin concentration in urine (creatinine correction value) with the putative glomerular filtration rate in accordance with staging of diabetic nephropathy in cases of stages-I to III diabetic nephropathy (68 cases).

FIG. 5 shows the correlation between the amount of albumin excreted into the urine (creatinine correction value) and the amount of megalin excreted into the urine (creatinine correction value). As shown in FIG. 5, the cases exhibiting the abnormally high amount of megalin excreted into the urine FIG. 6 shows the correlation between the putative glomerular filtration rate and the amount of megalin excreted into the urine. The term "glomerular filtration rate" refers to the amount of blood plasma filtered through all glomeruli in the kidney per unit time. The putative glomerular filtration rate (eGFR) can be determined by the equation shown below using the creatinine concentration in the serum, age, and sexuality as factors:

$$eGFR(ml/min/1.73\ m^2) = 194 \times Cr^{-1.094} \times Age^{-0.287} \times 0.739\ (if\ female)$$

The putative glomerular filtration rate is an indicator for evaluation of renal functions employed for a primary screening test for many chronic renal diseases, such as diabetic nephropathy or IgA nephropathy. According to the staging of chronic renal diseases, eGFR of 60 to 89 (ml/min/1.73 m$^2$) is evaluated as indicating a mild reduction in renal functions, that of 30 to 59 (ml/min/1.73 m$^2$) is evaluated as indicating a moderate reduction in renal functions, that of 15 to 29 (ml/min/1.73 m$^2$) is evaluated as indicating a severe reduction in renal functions, and that of lower than 15 (ml/min/1.73 m$^2$) is evaluated as indicating a renal failure. As shown in FIG. 6, the amount of megalin excreted into the urine tends to increase with a reduction in eGFR (i.e., reduction in renal functions), and the increased amount of megalin excreted into the urine has been found to be effective for accurate and early judgment of the degree of disorder (i.e., the progression of pathological conditions) of type II diabetic nephropathy.

Figure 7:
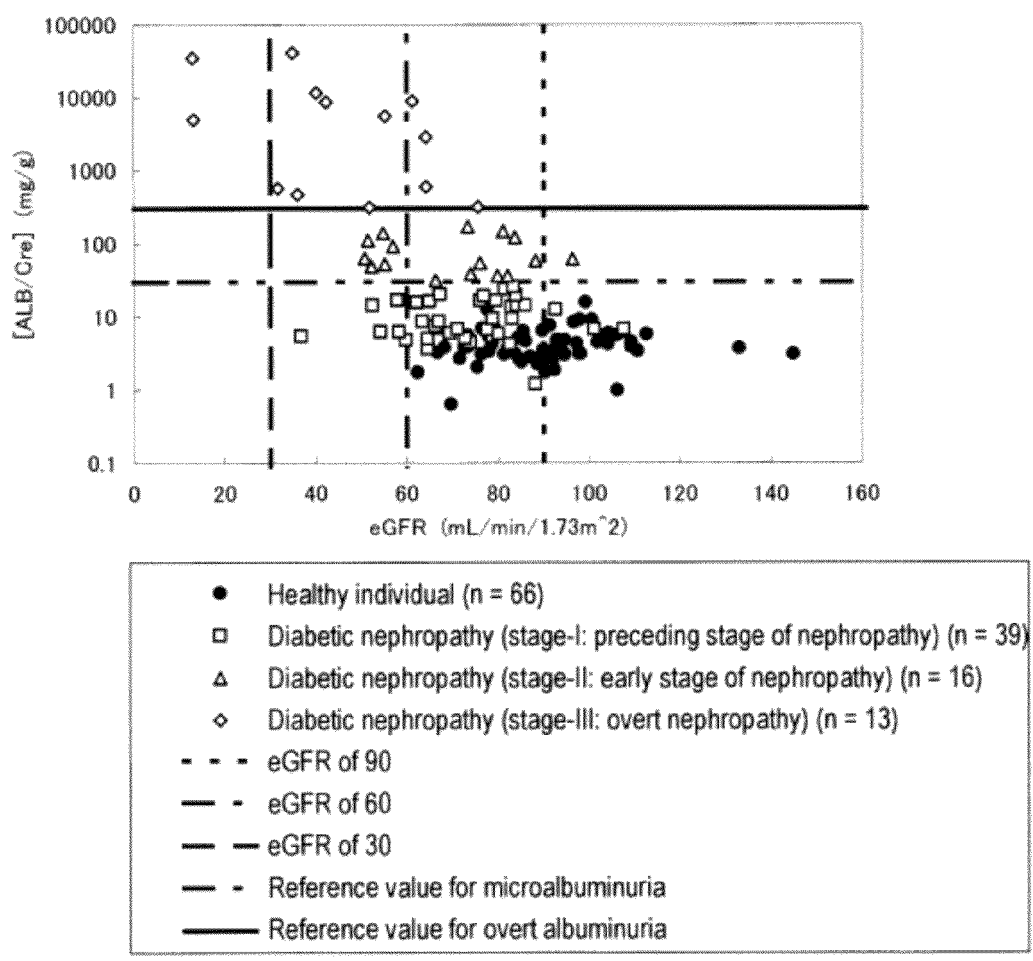
FIG. 7 shows the compatibility of the albumin concentration in urine (creatinine correction value) with the putative glomerular filtration rate in accordance with staging of diabetic nephropathy in cases of stages-I to III diabetic nephropathy (68 cases).

FIG. 7 shows the correlation between the putative glomerular filtration rate and the amount of albumin excreted into the urine. As shown in FIG. 7, the albumin level in urine tends to increase with a reduction in eGFR (i.e., a reduction in renal functions), as with the case of the amount of megalin excreted into the urine (FIG. 6). However, cases of normal albuminuria exhibiting eGFR of lower than 60 (ml/min/1.73 m$^2$) (i.e., renal dysfunction) and cases of microalbuminuria exhibiting eGFR of 90 or higher (ml/min/1.73 m$^2$) (i.e., normal renal functions) were observed. This indicates that the clinical significance (i.e., regarding accuracy of diagnosis) of albuminuria as a diagnostic marker for diabetic nephropathy is insufficient. The results demonstrate that use of megalin level in urine as an indicator for diagnosis of type II diabetic nephropathy enables more accurate diagnosis than is possible with the use of albuminuria.

The usefulness of the megalin level in urine as a diagnostic marker for type II diabetic nephropathy as can be seen in FIG. 6 and FIG. 7 was compared with that of other diagnostic markers for renal diseases in order to test the compatibility thereof with the putative glomerular filtration rate. Specifically, the results regarding type II diabetic nephropathy were classified as: eGFR of 90 or higher (ml/min/1.73 m$^2$) (score 1); 60 to 89 (ml/min/1.73 m$^2$) (score 2); 30 to 59 (ml/min/1.73 m$^2$) (score 3); and 15 to 29 (ml/min/1.73 m$^2$) (score 4). This was based on the staging of chronic renal diseases in terms of the putative glomerular filtration rate. The outcomes were indicated by occurence ration of outcome which exhibited values equal to or higher than reference values (i.e., cut-off values) for each marker. In such a test, significant difference was determined by the Mann-Whitney U test and the results were evaluated. As control diagnostic urine markers for renal disorders, β2-microglobulin in urine (cut-off: 300 µg/g creatinine in urine), α1-microglobulin in urine (cut-off: 12 mg/g creatinine in urine), N-acetyl-β-D-glucosaminidase in urine (cut-off: 6 IU/g creatinine in urine), protein in urine (cut-off: 0.5 g/g creatinine in urine), and urinary albumin (cut-off: 30 mg/g creatinine in urine) were employed, and standard cut-off values commonly employed in routine medical care were employed for the control markers. The results are shown in Table 9.

TABLE 9

|  | vs. albuminuria (dominance/ recessiveness) | vs. albuminuria (significant difference) | Accurate P-value |
| --- | --- | --- | --- |
| Megalin in urine | Dominant | P < 0.01 | 0.0073 |
| β2-MG in urine | Codominant | NS | 0.8733 |
| α1-MG in urine | Codominant | NS | 0.5288 |
| NAG in urine | Dominant | P < 0.05 | 0.0106 |
| protein in urine | Dominant | P < 0.001 | 1.1E−11 |

As shown in Table 9, the megalin level in urine, N-acetyl-β-D-glucosaminidase, and urinary protein were found to be more effective in terms of compatibility with the putative glomerular filtration rate, in comparison with the amount of albumin in urine, which is the most common diagnostic urine marker for diabetic nephropathy. The results of analysis demonstrated in this example (shown in Table 9) reflect stages-I to III diabetic nephropathy (i.e., from preceding stage of nephropathy to overt nephropathy). From the viewpoint of early diagnosis, attention should be paid to stages-I and II diabetic nephropathy (i.e., from preceding stage of nephropathy to early stage of nephropathy). This was described in Example 4.

Example 6

Comparison of Compatibility of Human Megalin in Urine and Other Markers for Renal Diseases with the Putative Glomerular Filtration Rate in Stages-I and II Diabetic Nephropathy (56 Cases), Taking Early Diagnosis of Renal Disease into Consideration (Significant Difference Test)

By paying attention to stages-I and II of diabetic nephropathy (i.e., from preceding stage of nephropathy to early stage of nephropathy), the usefulness of the megalin level in urine as a diagnostic marker for type II diabetic nephropathy as can be seen in FIG. 6 and FIG. 7 was compared with that of other diagnostic markers for renal diseases in terms of compatibility with the putative glomerular filtration rate. Specifically, the results regarding type II diabetic nephropathy were classified as: eGFR of 90 or higher (ml/min/1.73 m$^2$) (score 1), 60 to 89 (ml/min/1.73 m$^2$) (score 2), 30 to 59 (ml/min/1.73 m$^2$) (score 3), and 15 to 29 (ml/min/1.73 m$^2$) (score 4), based on the staging of chronic renal diseases in terms of the putative glomerular filtration rate. The outcomes were indicated by occurence ration of outcome which exhibited values equal to or higher than reference values (i.e., cut-off values) for each marker. Significant difference was determined by the Mann-Whitney U test and the results were evaluated. As control diagnostic urine markers for renal disorders, β2-microglobulin in urine (cut-off: 300 µg/g creatinine in urine), α1-microglobulin in urine (cut-off: 12 mg/g creatinine in urine), N-acetyl-β-D-glucosaminidase in urine (cut-off: 6 IU/g creatinine in urine), urinary protein (cut-off: 0.5 g/g creatinine in urine), and albumin in urine (cut-off: 30 mg/g creatinine in urine) were employed, and reference values commonly used in routine medical care were employed as cut-off values for control markers. The results are shown in Table 10.

TABLE 10

|  | vs. albuminuria (dominance/ recessiveness) | vs. albuminuria (significant difference) | Accurate P-value |
| --- | --- | --- | --- |
| Megalin in urine | Dominant | P < 0.01 | 0.0060 |
| β2-MG in urine | Codominant | NS | 0.0810 |
| α1-MG in urine | Codominant | NS | 0.1245 |
| NAG in urine | Codominant | NS | 0.0649 |
| Protein in urine | Codominant | NS | 0.1273 |

As shown in Table 10, the megalin level in urine alone was found to be more effective in terms of compatibility with the putative glomerular filtration rate, in comparison with the urinary albumin level, which is the most common diagnostic urine marker for diabetic nephropathy at present. Use of megalin level in urine as a diagnostic marker for type II diabetic nephropathy enables prognostic prediction of type II diabetic nephropathy and accurate and early judgment of the degree of disorder (i.e., the progression of pathological conditions), and such use is thus considered to be useful from the viewpoint of preventive medical care at an earlier stage.

Example 7

Figure 8:
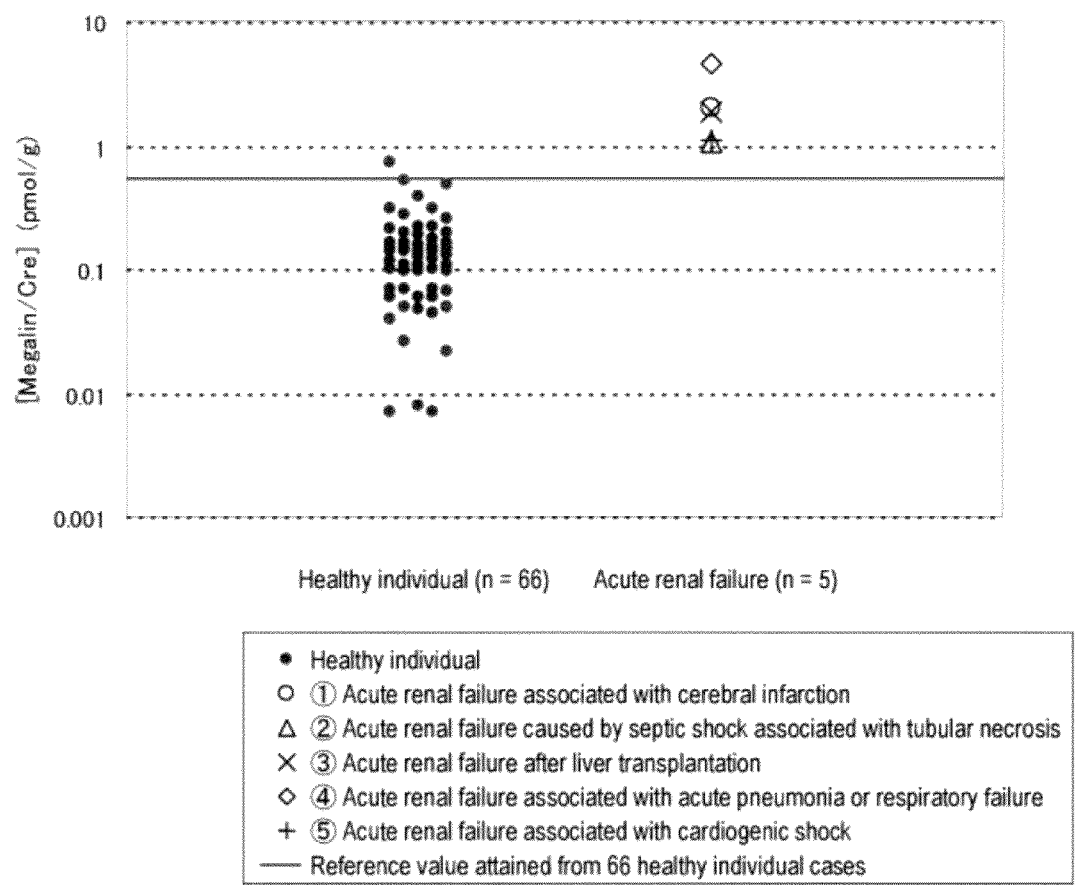
FIG. 8 shows the results of measurement of the amount of human megalin excreted into the urine (creatinine correction value) in cases of patients with acute renal failure. Underlying diseases of the acute renal disorder group (5 cases) are: 1: cerebral infarction; 2: septic shock caused by intestinal necrosis; 3: liver transplantation; 4: acute pneumonia and respiratory failure; and 5: cardiogenic shock.

Measurement of Amount of Human Megalin Excreted to Urine of Patient with Acute Renal Failure As shown in FIG. 8, the amount of megalin excreted into the urine was found to have increased significantly in the acute renal failure group, compared with healthy individuals. Acute renal failure was diagnosed in accordance with the relevant international standards (i.e., the RIFLE classification). The amount of megalin excreted into the urine was evaluated with the use of the creatinine correction value determined by dividing the megalin concentration in urine by the creatinine concentration in urine and correcting the concentration. The aforementioned is commonly used as a urinary biomarker in order to verify that the results are not influenced by the concentration rate at the time of urinary excretion. As a reference value for the amount of megalin excreted into the urine obtained from 66 healthy individuals (i.e., the normal range), 448 fmol (megalin in urine)/g (creatinine in urine) was employed. That is, a 95% confidence interval was calculated based on the normal distribution of megalin concentrations in urine of 66 healthy individuals (i.e., the creatinine correction value), the upper limit of the 95% confidence interval was 448 fmol (megalin in urine)/g (creatinine in urine), and the determined value was used as a reference value for the megalin concentrations in urine. It should be noted that the reference value obtained may vary depending on modification of methods for setting standards for the measurement platform or reference material, and the obtained value would not be permanently used as an absolute cut-off value. Specifically, the cut-off value is not particularly limited to 448 fmol (megalin in urine)/g (creatinine in urine). However, the results attained in this example can be conceived as a reference value with consistent validity. In this example, human megalin in urine was specifically measured and evaluated, and an increased amount of human megalin excreted into the urine was observed in patients with acute renal failure. Thus, human megalin in urine was considered to be effective for recognition of pathological conditions and diagnosis of nephropathy.

All publications, patents, and patent applications cited herein are incorporated herein by reference in their entirety.

INDUSTRIAL APPLICABILITY

By measuring the amount of megalin excreted into the urine of a patient with a renal disorder, and in particular, diabetic nephropathy, IgA nephropathy, nephrotic syndrome, chronic glomerulonephritis, membranous nephropathy, ANCA-associated glomerulonephritis, systemic erythematodes (lupus glomerulonephritis), Henoch-Schönlein purpura nephritis, interstitial glomerulonephritis, crescentic glomerulonephritis, focal glomerulosclerosis, nephrosclerosis, acute renal failure, chronic renal failure, renal amyloidosis, scleroderma renal crisis, interstitial glomerulonephritis caused by Sjogren's syndrome, or drug nephropathy, the activity of progressive renal disorder (e.g., the degree of progression or prognosis) can be evaluated. In order to inhibit the development and progression of nephropathy, lesions and the degree of the renal disorder are evaluated, and active treatment based on evidence is necessary. An increased amount of megalin excreted into the urine can be used for the evaluation of the degrees of proximal renal tubular disorders and failure of the resorption capacity at a lesion. Existing diagnostic markers for renal disorders do not enable determination regarding the lesions of renal disorders or evaluation of the functions in such lesions.

The increased amount of megalin excreted into the urine is observed at an early stage of nephropathy, and thus it is more effective for diagnosis of a renal disorder at an earlier stage than existing diagnostic markers for renal disorders. Based on the amount of megalin in urine, accordingly, the lesion and the degree of disorder can be determined with higher accuracy at an earlier stage, compared with the use of existing diagnostic markers for renal disorders. Accordingly, the amount of megalin in urine is effective for prognostic prediction of a renal disorder and accurate and early judgment of the degree of disorder (i.e., the progression of pathological conditions), and it is useful from the viewpoint of preventive treatment at an earlier stage.

The invention claimed is:

1. A method for detecting and treating a renal disorder in a subject, the method comprises:
    (i) measuring a human megalin level in a urine sample;
    (ii) determining the status or the degree of the renal disorder based on the human megalin level of step (i), wherein an increased level of human meglin comparing to a normal healthy subject indicates the renal disorder; and
    (iii) treating the subject with a suitable therapy based on the status or the degree of the renal disorder determined by step (ii),
wherein the renal disorder is selected from the group consisting of diabetic nephropathy, IgA nephropathy, acute renal failure, nephritic syndrome, chronic glomerulonephritis, membranous nephropathy, ANCA-associated glomerulonephritis, lupus glomerulonephritis, Henoch-Schönlein purpura nephritis, crescentic glomerulonephritis, focal glomerulosclerosis, acute renal failure, chronic renal failure, scleroderma renal crisis, post-transplant renal disorder, and interstitial glomerulonephritis caused by Sjogren's syndrome.

2. The method according to claim 1, wherein the renal disorder is detected for prognostic prediction.

3. The method according to claim 2, wherein the prognostic prediction of a renal disorder is performed to evaluate tubular dysfunctions.

4. The method according to claim 1, wherein the renal disorder is detected to evaluate the degree of disorder.

5. The method according to claim 4, wherein the degree of renal disorder is evaluated to evaluate tubular dysfunctions.

* * * * *

UNITED STATES PATENT AND TRADEMARK OFFICE
CERTIFICATE OF CORRECTION

| | | |
|---|---|---|
| PATENT NO. | : 8,628,930 B2 | Page 1 of 1 |
| APPLICATION NO. | : 13/266397 | |
| DATED | : January 14, 2014 | |
| INVENTOR(S) | : Akihiko Saito et al. | |

It is certified that error appears in the above-identified patent and that said Letters Patent is hereby corrected as shown below:

Title Page:

Please change the second assignee information, (item 73) from: "Juntendo Education Foundation" to: -- Juntendo Educational Foundation --.

Signed and Sealed this
Fifteenth Day of April, 2014

Michelle K. Lee
*Deputy Director of the United States Patent and Trademark Office*